(12) United States Patent
Misra et al.

(10) Patent No.: US 10,098,897 B2
(45) Date of Patent: Oct. 16, 2018

(54) METHODS AND MATERIALS FOR REDUCING DEVELOPMENT OF STENOSIS OF ARTERIOVENOUS FISTULAS

(71) Applicant: Mayo Foundation for Medical Education and Research, Rochester, MN (US)

(72) Inventors: Sanjay Misra, Rochester, MN (US); Rajiv Kumar, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 15/326,914

(22) PCT Filed: Jul. 17, 2015

(86) PCT No.: PCT/US2015/040976
§ 371 (c)(1),
(2) Date: Jan. 17, 2017

(87) PCT Pub. No.: WO2016/011397
PCT Pub. Date: Jan. 21, 2016

(65) Prior Publication Data
US 2017/0209466 A1 Jul. 27, 2017

Related U.S. Application Data

(60) Provisional application No. 62/025,897, filed on Jul. 17, 2014.

(51) Int. Cl.
*A61K 31/593* (2006.01)
*A61K 9/51* (2006.01)

(52) U.S. Cl.
CPC .......... *A61K 31/593* (2013.01); *A61K 9/5153* (2013.01)

(58) Field of Classification Search
CPC ................................................. A61K 31/593
USPC ...................................................... 514/167
See application file for complete search history.

(56) References Cited

U.S. PATENT DOCUMENTS

| 6,521,608 | B1 * | 2/2003 | Henner | A61K 31/593 514/167 |
| 2007/0148205 | A1 * | 6/2007 | Whitehouse | A61K 9/1075 424/423 |
| 2014/0011822 | A1 | 1/2014 | Misra | |

OTHER PUBLICATIONS

Gajendiran et al., J. Mat. Chem. B (2014), vol. 2, pp. 418-427 (published online Oct. 31, 2013).*
Al-Jaishi et al., "Patency rates of the arteriovenous fistula for hemodialysis: a systematic review and meta-analysis," *Am. J. Kidney Dis.*, 63(3):464-478, Mar. 2014.
Beer et al., *J. Clin. Oneal.*, 25:669-674, 2007.
Beer et al., *Semin. Oneal.*, 28:49-55, 2001.
Brahmbhaat et al, "The Role of Iex-1 in the Pathogenesis of Venous Neointimal Hyperplasia Associated with Hemodialysis Arteriovenous Fistula," *PLoS ONE.*, 9(7):1-13, Jul. 18, 2014.
GenBank accession No. AA039405.1 (GI No. 37726925), "gly96 protein [*Mus musculus*]," Jul. 26, 2016, 1 page.
GenBank accession No. Np 003888.2, (GI No. 119964723), "radiation-inducible immediate-early gene IEX-1 [*Homo sapiens*]," Jun. 4, 2017, 3 pages.
Howard Hughes Medical Institute 2014 Scientific Meeting of Medical Fellows, May 19, 2014, p. 25, first column.
Im et al., "Characterization of a novel hexameric repeat DNA sequence in the promoter of the immediate early gene, IEX-1, that mediates 1alpha,25-dihydroxyvitamin D3-associated IEX-1 gene repression," *Oncogene.*, 21(23):3706-3714, May 23, 2002.
International Preliminary Report on Patentability of International Application No. PCT/US2015/040976, dated Jan. 17, 2017, 6 pages.
International Search Report and Written Opinion of International Application No. PCT/US2015/040976, dated Oct. 26, 2015, 12 pages.
Janardhanan et al., "Simvastatin reduces venous stenosis formation in a murine hemodialysis vascular access model," *Kidney Int.*, 84(2):338-352, Aug. 2013.
Misra et al., "Increased expression of HIF-1alpha, VEGF-A and its receptors, MMP-2, TIMP-1, and ADAMTS-1 at the venous stenosis of arteriovenous fistula in a mouse model with renal insufficiency," *J. Vasc. Interv. Radiol.*, 21(8):1255-1261, Aug. 2010.
Misra et al., "Hypoxia induces a phenotypic switch of fibroblasts to myofibroblasts through a MMP-2/TIMP mediated pathway: Implications for venous neointimal hyperplasia in hemodialysis access," *J. Vasc. Interv. Radial.*, 21(6):896-902, 2010.
Misra et al., "Adventitial remodeling with increased matrix metalloproteinase-2 activity in a porcine arteriovenous polytetrafluoroethylene grafts," *Kidney Int.*, 68(6):2890-2900, Dec. 2005.
Nieves et al., "Adventitial Delivery of Lentivirus-shRNA-ADAMTS-1 Reduces Venous Stenosis Formation in Arteriovenous Fistula," *PLoS One*, 9(4): e94510, 13 pages, Apr. 2014.
Rooijens et al., "Radiocephalic wrist arteriovenous fistula for hemodialysis: meta-analysis indicates a high primary failure rate," *Eur. J. Vase. Endovasc. Surg.*, 28(6):583-589, Dec. 2004.
Roy-Chaudhury et al., "Hemodialysis Vascular Access Dysfunction: A Cellular and Molecular Viewpoint," *J. Am. Soc. Nephrol.*, 17(4): 1112-1127, 2006.
Riella & Roy-Chaudhury, Vascular access in haemodialysis: strengthening the Achilles' heel, *Nat. Rev. Nephrol.*, 9:348-357, Jun. 2013.
Schulze et al., "Biomechanically Induced Gene iex-1 Inhibits Vascular Smooth Muscle Cell Proliferation and Neointima Formation," *Circ. Res.*, 93:1210-1217, 2003.
Sommer et al., "Elevated blood pressure and cardiac hypertrophy after ablation of the gly96/IEX-1 gene," *J. Appl. Physiol.*, 100(2):707-716, Feb. 1, 2006.

(Continued)

*Primary Examiner* — Taofiq A Solola
(74) *Attorney, Agent, or Firm* — Fish & Richardson P.C.

(57) ABSTRACT

This document provides methods and materials for reducing development of stenosis of arteriovenous fistulas. For example, methods and materials for reducing IEX-1 polypeptide expression or activity within a mammal (e.g., a human) to reduce venous neointimal hyperplasia and/or the development of stenosis of arteriovenous fistulas are provided.

14 Claims, 15 Drawing Sheets
Specification includes a Sequence Listing.

(56) References Cited

OTHER PUBLICATIONS

Wang et al., "Identification of Immediate Early Gene X-1 as a Cellular Target Gene of Hcmv-Mir-U1148d," *Int. J. Mol. Med.*, 31(4):959-966, Feb. 6, 2013.

Wang et al., "Venous stenosis in a pig arteriovenous fistula model anatomy, mechanisms and cellular phenotypes," *Nephrol. Dial. Transplant.*, 22:3139-3146, 2007.

Yang et al., "The Mouse Arteriovenous Fistula Model," *J. Vasc. Interv. Radial.*, 20(7):946-950, 2009.

Yang et al., "Adventitial transduction of lentivirus-shRNA-VEGF-A in arteriovenous fistula reduces venous stenosis formation," *Kidney Int.*, 85:289-306, 2014.

Argiriou et al., "Creating arteriovenous fistula using an automatic anastomotic device," *J Vascular Surgery.*, 53(2):531-533, Feb. 2011.

Brahmbhatt et al., "The molecular mechanisms of hemodialysis vascular access failure," *Kidney International.*, 89:303-316, 2016.

Misra et al., "Assessment of Wall Shear Stress Changes in Arteries and Veins of Arteriovenous Polytetrafluoroethylene Grafts Using Magnetic Resonance Imaging," *Cardiovasc Intervent Radiol.*, 29:624-629, 2006.

\* cited by examiner

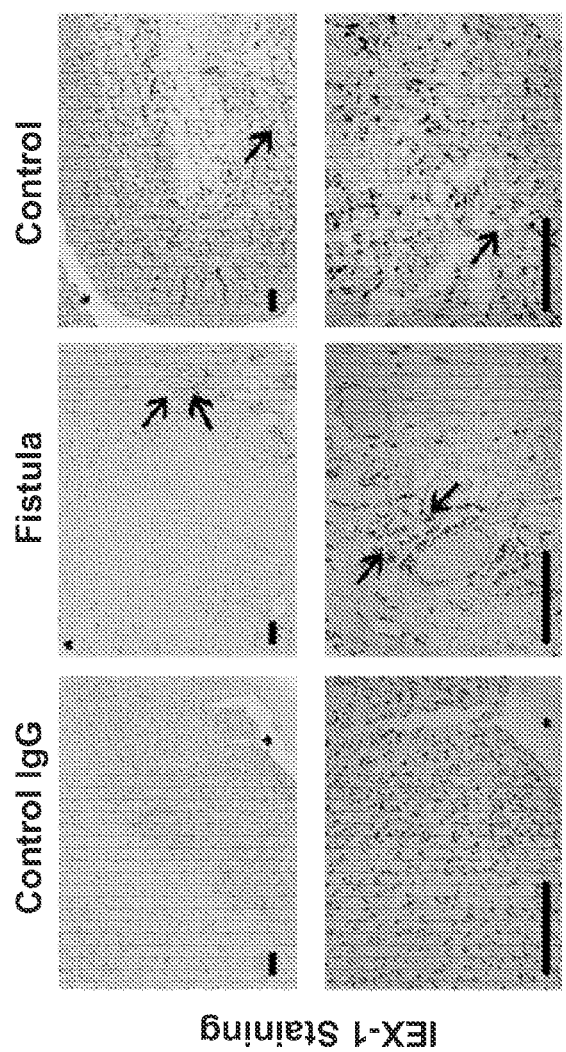
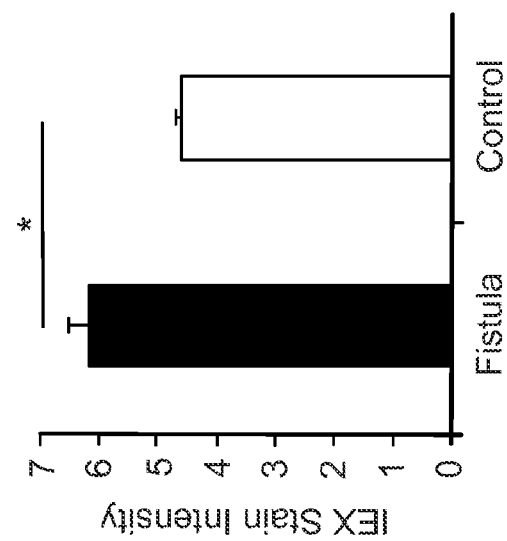
FIG. 1A
FIG. 1B

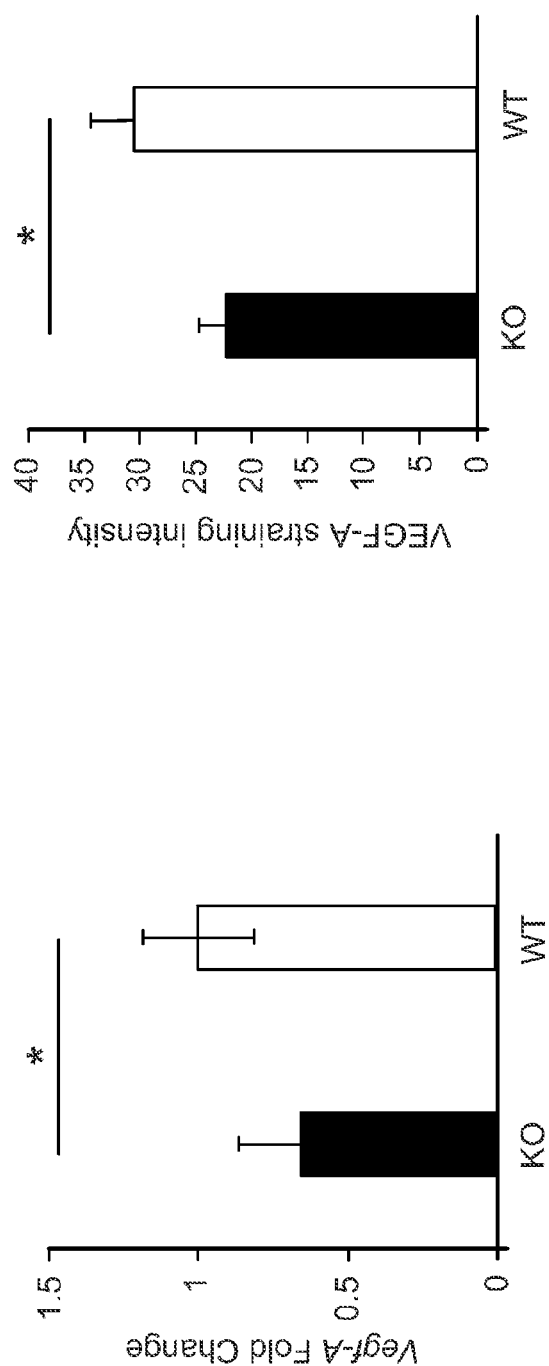
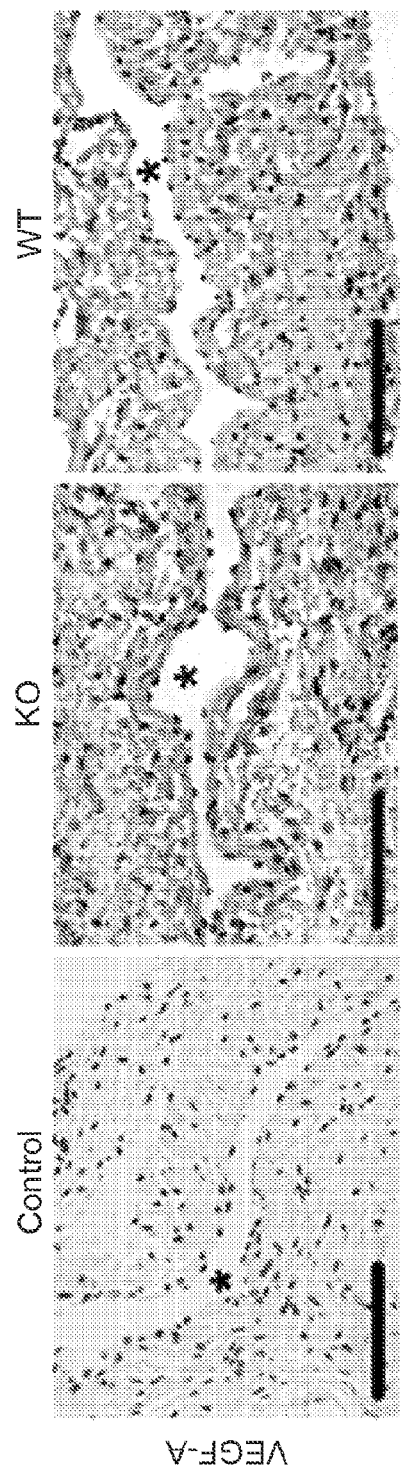
FIG. 2A
FIG. 2B
FIG. 2C

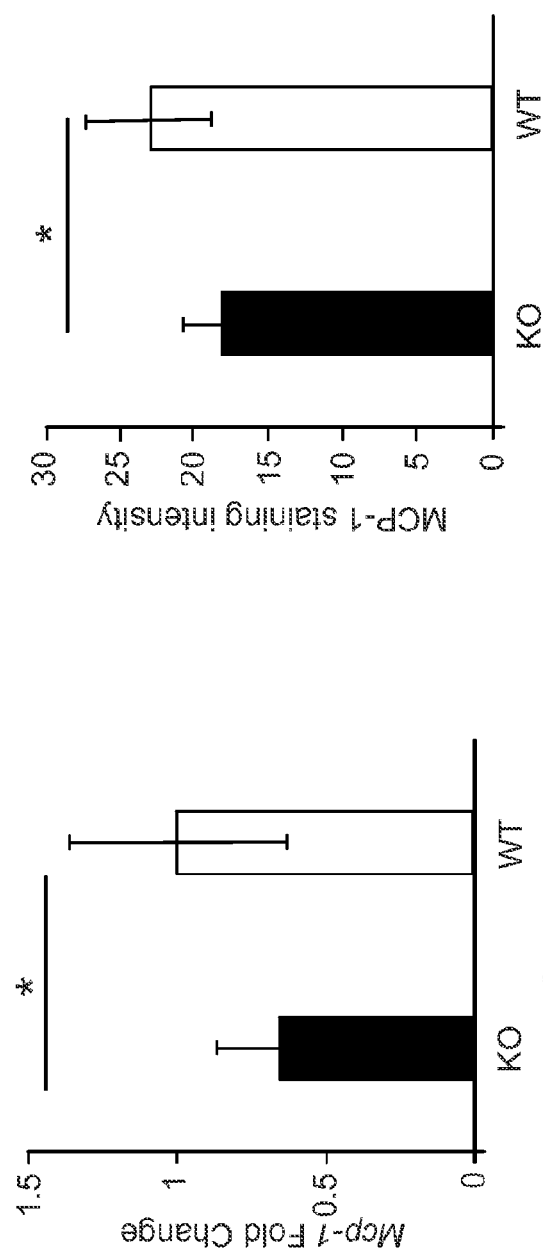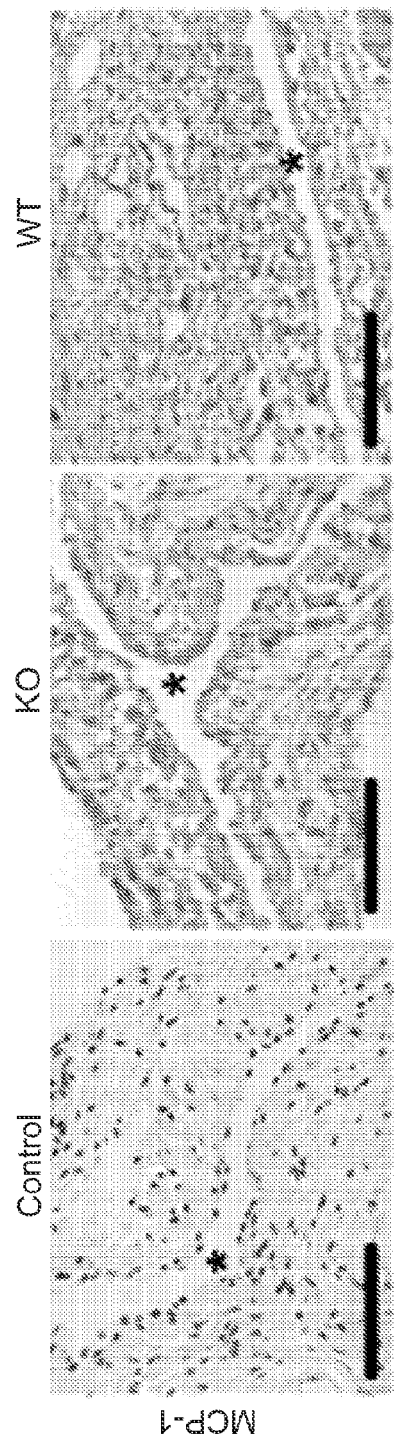

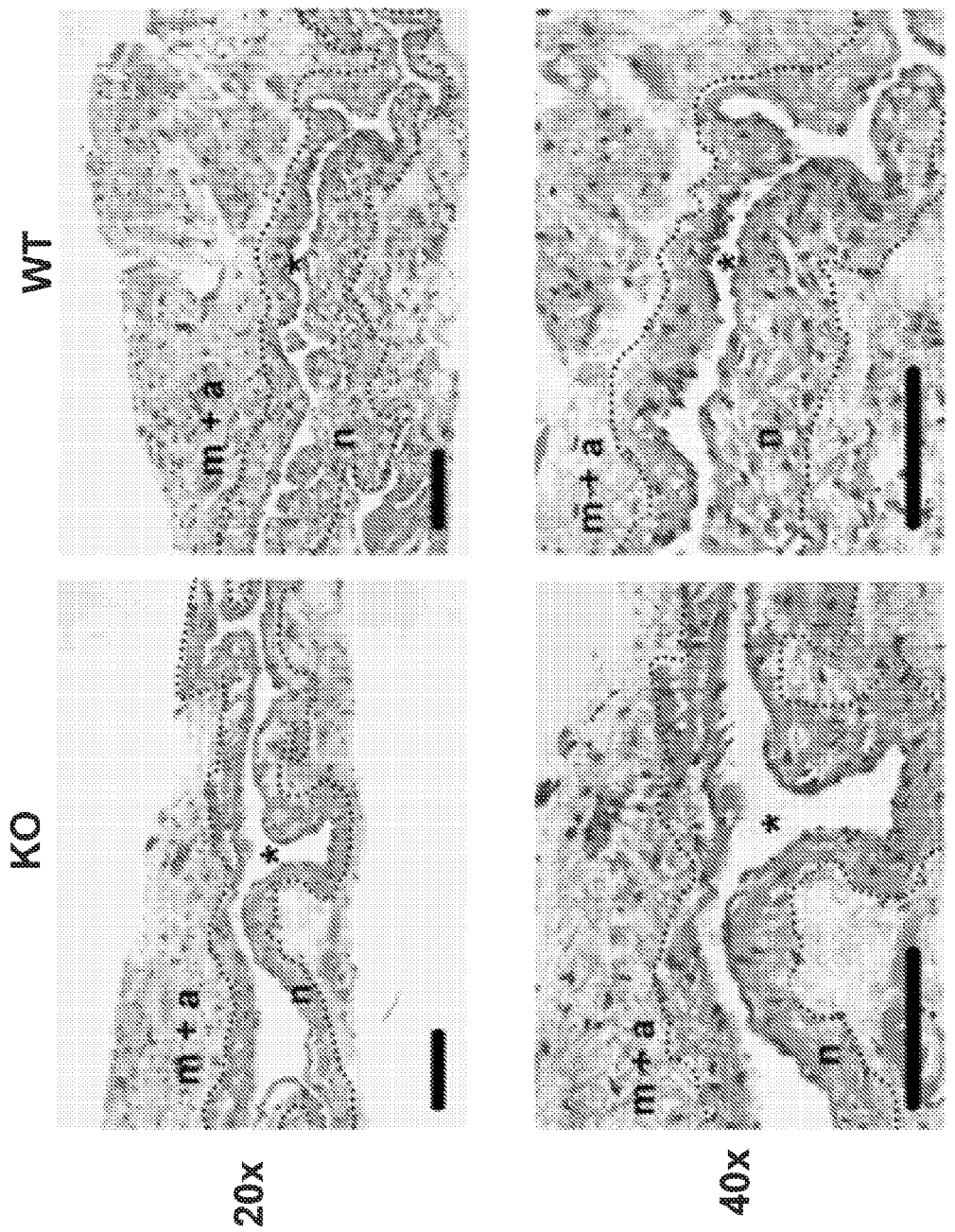

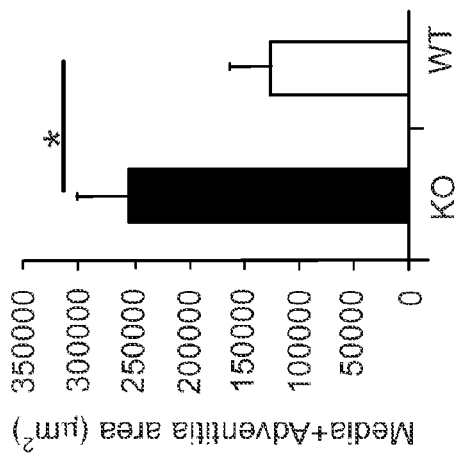
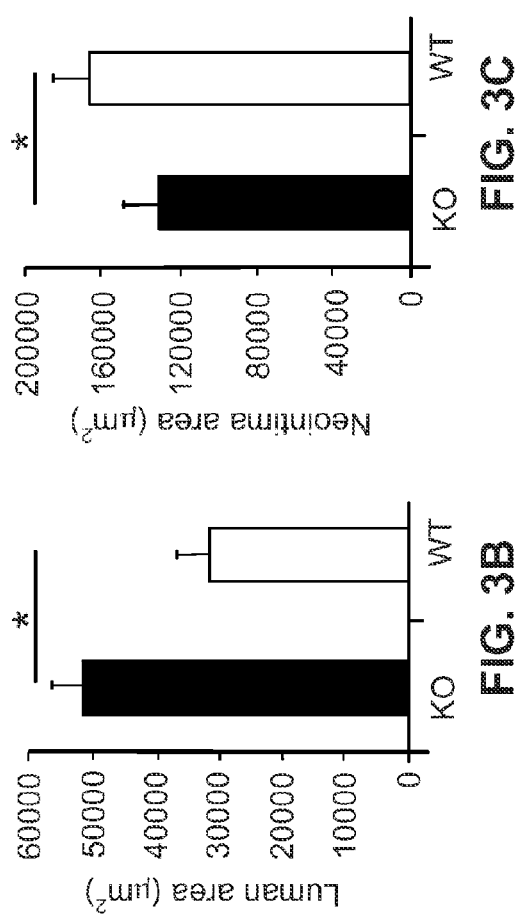
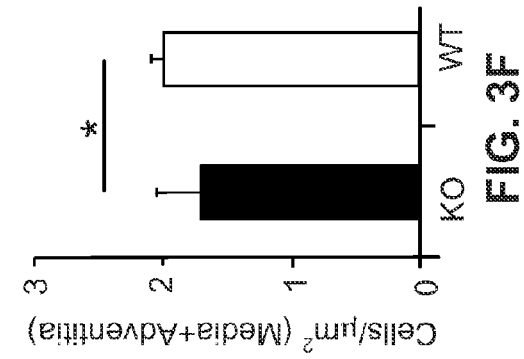
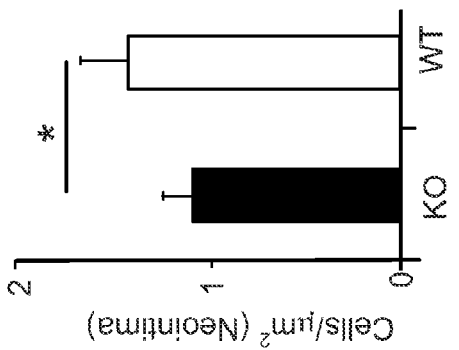

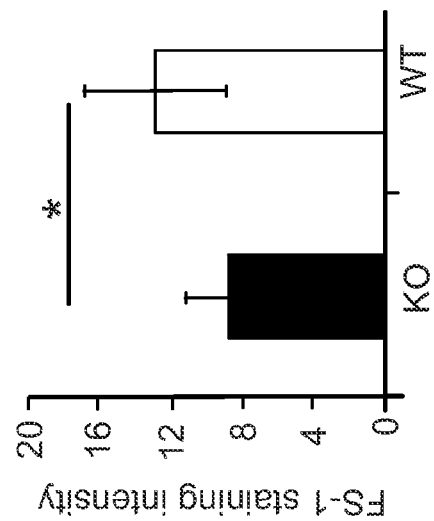
FIG. 4A
FIG. 4B

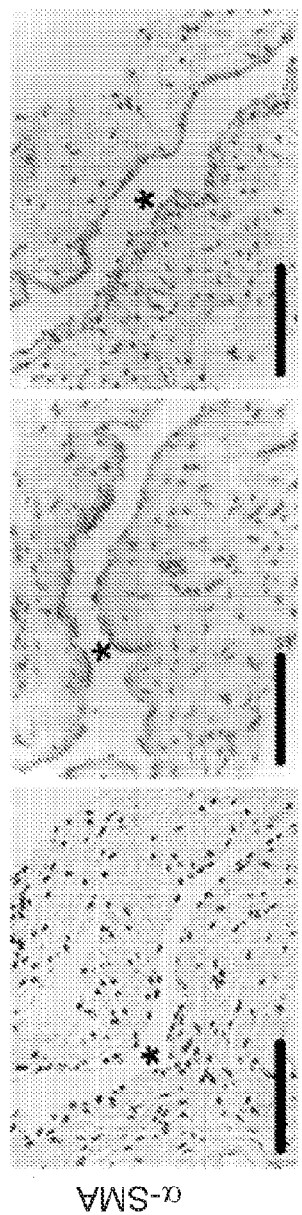
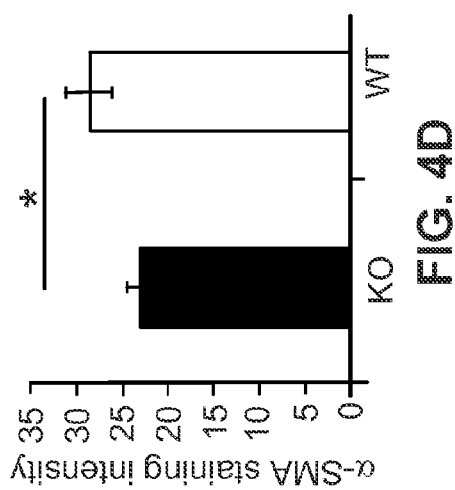
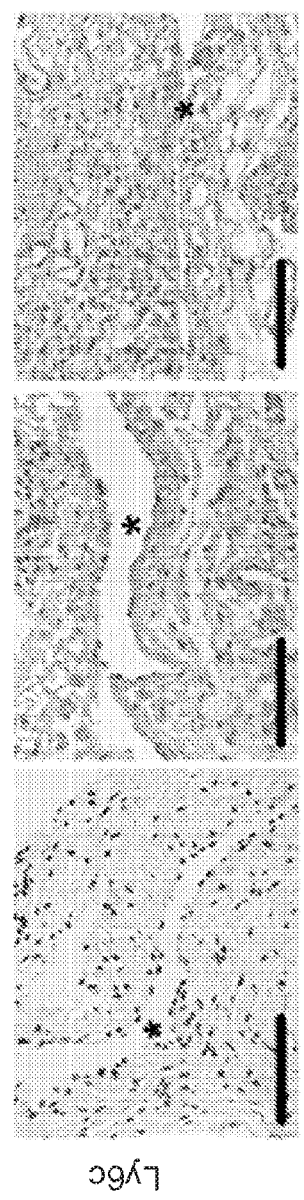
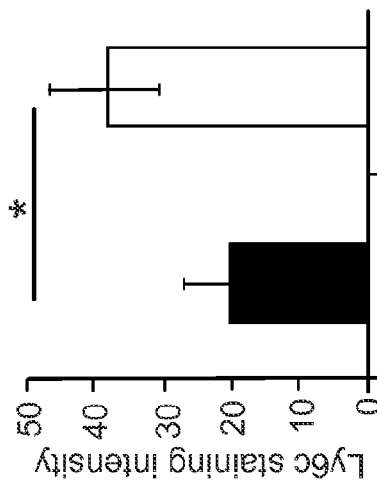

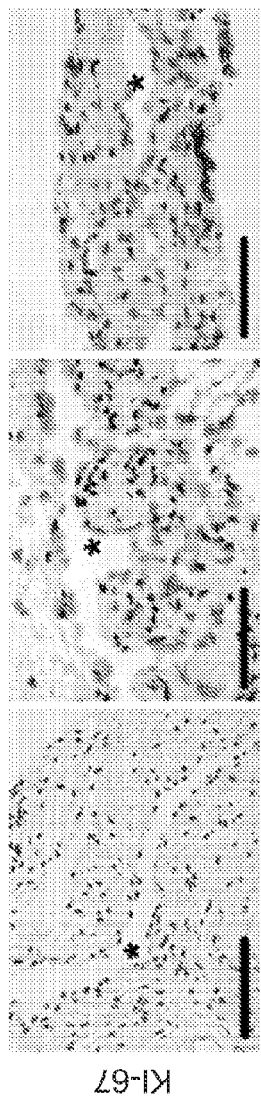
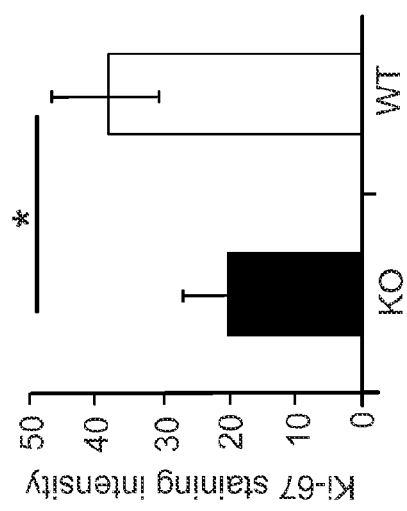
FIG. 4G
FIG. 4H
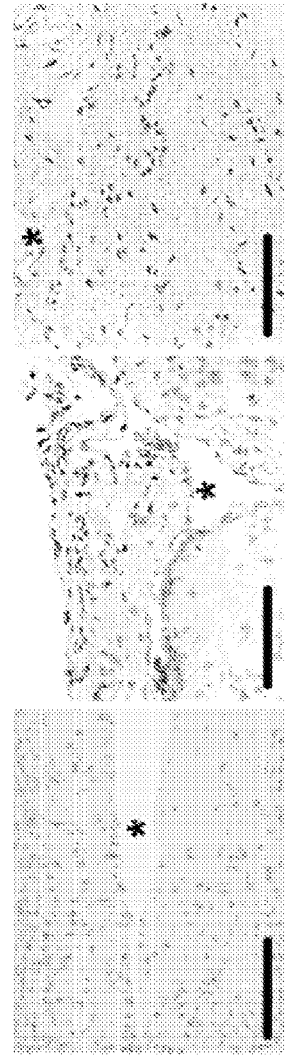
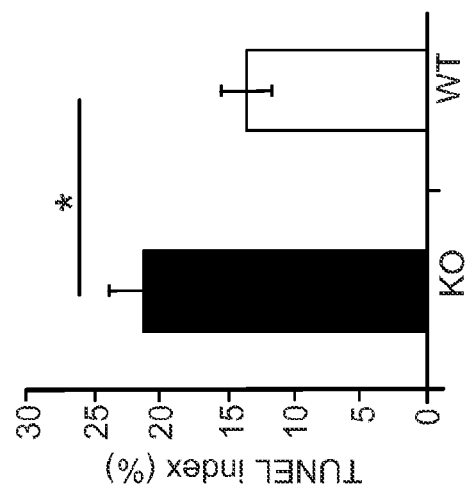
FIG. 4I
FIG. 4J

SEQUENCE LISTING

```
<160> NUMBER OF SEQ ID NOS: 30

<210> SEQ ID NO 1
<211> LENGTH: 19
<212> TYPE: DNA
<213> ORGANISM: Homo sapiens

<400> SEQUENCE: 1
atgtgtcact ctcgcagct                                                   19

<210> SEQ ID NO 2
<211> LENGTH: 19
<212> TYPE: DNA
<213> ORGANISM: Homo sapiens
```

-continued

```
<400> SEQUENCE: 2
gctccggtcc tgagatctt                                                19

<210> SEQ ID NO 3
<211> LENGTH: 19
<212> TYPE: DNA
<213> ORGANISM: Homo sapiens

<400> SEQUENCE: 3
tctttctgct gctcaccat                                                19

<210> SEQ ID NO 4
<211> LENGTH: 19
<212> TYPE: DNA
<213> ORGANISM: Homo sapiens

<400> SEQUENCE: 4
cctttaatct gacttcgga                                                19

<210> SEQ ID NO 5
<211> LENGTH: 19
<212> TYPE: DNA
<213> ORGANISM: Homo sapiens

<400> SEQUENCE: 5
gcactttcct ccagcaaca                                                19

<210> SEQ ID NO 6
<211> LENGTH: 19
<212> TYPE: DNA
<213> ORGANISM: Homo sapiens

<400> SEQUENCE: 6
atgtgtcact ctcgcagct                                                19

<210> SEQ ID NO 7
<211> LENGTH: 20
<212> TYPE: DNA
<213> ORGANISM: Homo sapiens

<400> SEQUENCE: 7
gctccggtcc tgagatcttc                                               20

<210> SEQ ID NO 8
<211> LENGTH: 19
<212> TYPE: DNA
<213> ORGANISM: Homo sapiens

<400> SEQUENCE: 8
tctttctgct gctcaccat                                                19

<210> SEQ ID NO 9
<211> LENGTH: 19
<212> TYPE: DNA
<213> ORGANISM: Homo sapiens

<400> SEQUENCE: 9
cctttaatct gacttcgga                                                19

<210> SEQ ID NO 10
<211> LENGTH: 19
<212> TYPE: DNA
<213> ORGANISM: Homo sapiens
```

```
<400> SEQUENCE: 10
gcactttcct ccagcaaca                                                   19

<210> SEQ ID NO 11
<211> LENGTH: 19
<212> TYPE: DNA
<213> ORGANISM: Mus musculus

<400> SEQUENCE: 11
gcaaccatct ccacaccat                                                   19

<210> SEQ ID NO 12
<211> LENGTH: 19
<212> TYPE: DNA
<213> ORGANISM: Mus musculus

<400> SEQUENCE: 12
tccaccgcgc gtttgaaca                                                   19

<210> SEQ ID NO 13
<211> LENGTH: 19
<212> TYPE: DNA
<213> ORGANISM: Mus musculus

<400> SEQUENCE: 13
tcgccatcat cttctgcca                                                   19

<210> SEQ ID NO 14
<211> LENGTH: 19
<212> TYPE: DNA
<213> ORGANISM: Mus musculus

<400> SEQUENCE: 14
actatgcgct ggatcttaa                                                   19

<210> SEQ ID NO 15
<211> LENGTH: 19
<212> TYPE: DNA
<213> ORGANISM: Mus musculus

<400> SEQUENCE: 15
aacatccggc ggcctctta                                                   19

<210> SEQ ID NO 16
<211> LENGTH: 19
<212> TYPE: DNA
<213> ORGANISM: Mus musculus

<400> SEQUENCE: 16
gcaaccatct ccacaccat                                                   19

<210> SEQ ID NO 17
<211> LENGTH: 19
<212> TYPE: DNA
<213> ORGANISM: Mus musculus

<400> SEQUENCE: 17
tccaccgcgc gtttgaaca                                                   19

<210> SEQ ID NO 18
<211> LENGTH: 19
<212> TYPE: DNA
```

<213> ORGANISM: Mus musculus

<400> SEQUENCE: 18
tcgccatcat cttctgcca                          19

<210> SEQ ID NO 19
<211> LENGTH: 19
<212> TYPE: DNA
<213> ORGANISM: Mus musculus

<400> SEQUENCE: 19
actatgcgct ggatcttaa                          19

<210> SEQ ID NO 20
<211> LENGTH: 19
<212> TYPE: DNA
<213> ORGANISM: Mus musculus

<400> SEQUENCE: 20
aacatccggc ggccttcta                          19

<210> SEQ ID NO 21
<211> LENGTH: 20
<212> TYPE: DNA
<213> ORGANISM: Mus musculus

<400> SEQUENCE: 21
agctaggaat aatggaatag                         20

<210> SEQ ID NO 22
<211> LENGTH: 21
<212> TYPE: DNA
<213> ORGANISM: Mus musculus

<400> SEQUENCE: 22
aatcaagaac gaaagtcgga g                       21

<210> SEQ ID NO 23
<211> LENGTH: 19
<212> TYPE: DNA
<213> ORGANISM: Mus musculus

<400> SEQUENCE: 23
gcgcgtttga acacttctc                          19

<210> SEQ ID NO 24
<211> LENGTH: 20
<212> TYPE: DNA
<213> ORGANISM: Mus musculus

<400> SEQUENCE: 24
atggcgaaca ggagaaagag                         20

<210> SEQ ID NO 25
<211> LENGTH: 26
<212> TYPE: DNA
<213> ORGANISM: Mus musculus

<400> SEQUENCE: 25 gttttttgatg ctattgctga gatcca                 26

<210> SEQ ID NO 26
<211> LENGTH: 25

```
<212> TYPE: DNA
<213> ORGANISM: Mus musculus

<400> SEQUENCE: 26
cccacatttg acgtccagag aagaa                                         25

<210> SEQ ID NO 27
<211> LENGTH: 19
<212> TYPE: DNA
<213> ORGANISM: Mus musculus

<400> SEQUENCE: 27
gtccctgtca tgcttctgg                                                19

<210> SEQ ID NO 28
<211> LENGTH: 20
<212> TYPE: DNA
<213> ORGANISM: Mus musculus

<400> SEQUENCE: 28
gctctccagc ctactcattg                                               20

<210> SEQ ID NO 29
<211> LENGTH: 21
<212> TYPE: DNA
<213> ORGANISM: Mus musculus

<400> SEQUENCE: 29
atgaagtgat caagttcatg g                                             21

<210> SEQ ID NO 30
<211> LENGTH: 21
<212> TYPE: DNA
<213> ORGANISM: Mus musculus

<400> SEQUENCE: 30
ggatcttgga caaacaaatg c                                             21
```

METHODS AND MATERIALS FOR REDUCING DEVELOPMENT OF STENOSIS OF ARTERIOVENOUS FISTULAS

CROSS REFERENCE TO RELATED APPLICATIONS

This application is a National Stage application under 35 U.S.C. § 371 of International Application No. PCT/US2015/040976, having an International Filing Date of Jul. 17, 2015, which claims the benefit of U.S. Provisional Ser. No. 62/025,897 filed Jul. 17, 2014. This disclosure of the prior application is considered part of (and is incorporated by reference in) the disclosure of this application.

STATEMENT AS TO FEDERALLY SPONSORED RESEARCH

This invention was made with government support under HL098967 awarded by National Institutes of Health. The government has certain rights in the invention.

BACKGROUND

1. Technical Field

This document relates to methods and materials for reducing development of stenosis of arteriovenous fistulas. For example, this document relates to reducing IEX-1 polypeptide expression or activity within a mammal to reduce development of stenosis of arteriovenous fistulas.

2. Background Information

There are more than 1,500,000 patients worldwide with end stage renal disease (ESRD). These patients require hemodialysis for removal of uremic toxins and control of volume. In order for effective hemodialysis to be performed, an optimally functioning hemodialysis vascular access is needed. An arteriovenous fistula (AVF) is the preferred vascular access for chronic hemodialysis because it has lower infection and thrombosis rates with increased patency when compared to polytetrafluoroethylene (PTFE) grafts (Roy-Chaudhury et al., *J. Am. Soc. Nephrol.*, 17:1112-1127 (2006) and Riella and Roy-Chaudhury, *Nat. Rev. Nephrol.*, 9:348-357 (2013)). AVF stenosis occurs at the outflow vein due to venous neointimal hyperplasia (VNH) with the one-year patency of AVFs being approximately 60% (Al-Jaishi et al., *Am. J. Kidney Dis.*, 63:464-478 (2014)). The stenosis requires frequent radiological and surgical intervention to prolong AVF function resulting in increased economic and health burden (Riella and Roy-Chaudhury, *Nat. Rev. Nephrol.*, 9:348-357 (2013) and Rooijens et al., *Eur. J. Vasc. Endovasc. Surg.*, 28:583-589 (2004)).

SUMMARY

This document provides methods and materials for reducing development of stenosis of arteriovenous fistulas. For example, this document relates to reducing IEX-1 polypeptide expression or activity within a mammal (e.g., a human) to reduce venous neointimal hyperplasia and/or the development of stenosis of arteriovenous fistulas. As described herein, administering a composition that reduces IEX-1 polypeptide expression or activity to a mammal can reduce venous neointimal hyperplasia and/or can reduce the development of stenosis of a hemodialysis vascular access (e.g., an AVF). In some cases, a composition that reduces IEX-1 polypeptide expression or activity can be administered to a mammal before or after placement of a hemodialysis vascular access (e.g., before or after creating an AVF) to reduce venous neointimal hyperplasia and/or to reduce the development of stenosis of the hemodialysis vascular access (e.g., the AVF). For example, a human patient requiring hemodialysis can undergo a surgical procedure to create an AVF. Prior to creating the AVF, an administration (e.g., an adventitial administration) of a composition that reduces IEX-1 polypeptide expression or activity can be performed to reduce venous neointimal hyperplasia and/or to reduce the development of stenosis of the AVF. In some cases, an administration (e.g., an adventitial administration) of a composition that reduces IEX-1 polypeptide expression or activity can be performed after the AVF is created or after an angioplasty procedure or after a stent placement procedure to reduce venous neointimal hyperplasia and/or to reduce the development of stenosis of a hemodialysis vascular access (e.g., an AVF). In some cases, a systemic or oral administration or local continuous infusion can be performed. In some cases, stenosis can be treated by delivering a composition that reduces IEX-1 polypeptide expression or activity to the endothelium using a drug coated balloon or drug infusing catheter to the endothelium, media, or adventitia.

Having the ability to reduce IEX-1 polypeptide expression or activity as described herein to reduce venous neointimal hyperplasia and/or the development of stenosis of a hemodialysis vascular access within a mammal can allow doctors to maintain effective hemodialysis vascular access for extended periods of time.

In general, one aspect of this document features a method for reducing the development of stenosis of an arteriovenous fistula within a mammal. The method comprises, or consists essentially of, administering a composition that reduces IEX-1 polypeptide expression or activity to the mammal, wherein the development of stenosis of the arteriovenous fistula is reduced following the administering step as compared to the level of arteriovenous fistula stenosis development within a mammal having an arteriovenous fistula and not administered the composition. The mammal can be a human. The composition can comprise calcitriol. The composition can comprise nanoparticles. The composition can comprise PLGA nanoparticles. Between about 5 and 95 percent of the composition can comprise calcitriol. The composition can further comprise gold particles or poly (lactic-co-glycolic acid). The administration can comprise an adventitial administration.

In another aspect, this document features a method for treating a mammal having an arteriovenous fistula. The method comprises, or consists essentially of, (a) identifying the mammal as having the arteriovenous fistula in need of developing less stenosis, and (b) administering a composition that reduces IEX-1 polypeptide expression or activity to the mammal, wherein the development of stenosis of the arteriovenous fistula is reduced following the administering step as compared to the level of arteriovenous fistula stenosis development within a mammal having an arteriovenous fistula and not administered the composition. The mammal can be a human. The composition can comprise calcitriol. The composition can comprise nanoparticles. The composition can comprise PLGA nanoparticles. Between about 5 and 95 percent of the composition can comprise calcitriol. The composition can further comprise gold particles or poly(lactic-co-glycolic acid). The administration can comprise an adventitial administration.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description and drawings, and from the claims.

DESCRIPTION OF DRAWINGS

FIG. 1: IEX-1 expression in malfunctioning AV fistulae when compared to controls removed from patients. Representative IEX-1 staining is shown in (a) on outflow veins removed from patients with malfunctioning AVF when compared to control veins removed from patients undergoing placement of a AVF. IEX-1 expression was localized to the adventitia (arrow heads) of AVF when compared to controls. Brown staining cells were positive for IEX-1. Top row is 10× and bottom row is 40×. Scale bar is 100 µms. * denotes vessel lumen. Pooled data from the semi-quantitative analysis for intensity of IEX-1 staining in the vessel wall of the outflow vein specimens removed from patients with AVF or controls is shown in (b). This demonstrates a significant increase in the mean IEX-1 expression in the AVF when compared to controls (P<0.05). Each bar shows the mean±SEM of 3 samples per group. Two-way Student t-test was performed. Significant difference from control value is indicated by * P<0.05.

FIG. 3: Hematoxylin and eosin staining with histomorphometric analysis of outflow vein removed from Iex-1$^{-/-}$ and WT animals at day 28 after fistula placement. Representative hematoxylin and eosin staining of the outflow vein removed from Iex-1 KO and WT mice from 28 days after fistula placement is shown in (a). The neointima (n) was identified from the media and adventitia by the dotted line. m+a is the media and adventitia. * denotes vessel lumen. Top row is 20×, and bottom row is 40×. Scale bar is 100 µms. Pooled data from the mean lumen vessel area from Iex-1 KO and WT animals are shown in (b). There was a significant increase in the mean lumen vessel area in the Iex-1 KO animals when compared to WT controls (P<0.05). Pooled data from the mean neointima area from Iex-1 KO and WT animals are shown in (c). There was a significant decrease in the mean area of the neointima in the Iex-1 KO animals when compared to WT controls (P<0.05). Pooled data from the mean area of the media and adventitia from Iex-1 KO and WT animals are shown in (d). There was a significant increase in the mean area of the media and adventitia in the Iex-1 KO animals when compared to WT controls (P<0.05). Pooled data from the mean cell density in the neointima from Iex-1 KO and WT animals are shown in (e). There was a significant decrease in the mean cell density of the neointima in the Iex-1 KO animals when compared to WT controls (P<0.05). Pooled data from the mean cell density in the media and adventitia from Iex-1 KO and WT animals are shown in (f). There was a significant increase in the mean cell density of the media and adventitia in the Iex-1 KO animals when compared to WT controls (P<0.05). Student t-test with post hoc Bonferroni's correction was performed. Significant difference from control value is indicated by * P<0.05. Each bar shows mean±SEM of 4-5 animals per group.

FIG. 4: There was a significant decrease in fibroblast, α-SMA, and Ly6C staining accompanied with a decrease in proliferation, and increase in cell death in the outflow vein removed Iex-1 KO mice when compared to WT controls at day 28 after fistula. (a) Representative staining for Fsp-1 from the outflow vein removed from Iex-1 KO (second column) and WT controls (third column) are shown. IgG antibody staining was performed to serve as negative control in the first column. Brown staining cells are positive for FSP-1. All images are 40×. Scale bar is 100 µms. * indicates lumen. (b) Pooled data from the semiquantitative analysis for intensity of Fsp-1 staining in the vessel wall of the outflow vein specimens removed from Iex-1 KO and WT mice are shown. There was a significant decrease in the mean FSP-1 staining in the Iex-1 KO animals when compared to WT controls (P<0.05). (c) Representative staining for α-SMA from the outflow vein removed from Iex-1 KO (second column) and WT controls (third column) IgG antibody staining was performed to serve as negative control in the first column. Brown staining cells are positive for α-SMA. (d) Pooled data from the semiquantitative analysis for intensity of α-SMA staining in the vessel wall of the outflow vein specimens removed from Iex-1 KO and WT mice are shown. There was a significant decrease in the mean α-SMA staining in the Iex-1 KO animals when compared to WT controls (P<0.05). (e) Representative staining for Ly6c from the outflow vein removed from Iex-1 KO (second column) and WT controls (third column) IgG antibody staining was performed to serve as negative control in the first column. Brown staining cells are positive for Ly6C. (f) Pooled data from the semiquantitative analysis for intensity of Ly6C staining in the vessel wall of the outflow vein specimens removed from Iex-1 KO and WT mice are shown. There was a significant decrease in the mean Ly6c staining in the Iex-1 KO animals when compared to WT controls (P<0.05). (g) Representative staining for Ki-67 from the outflow vein removed from Iex-1 KO (second column) and WT controls (third column) IgG antibody staining was performed to serve as negative control in the first column. Nuclei staining brown are positive for Ki-67. (h) Pooled data for the semiquantitative analysis for intensity of Ki-67 staining in the vessel wall of the outflow vein specimens removed from Iex-1 KO and WT mice are shown. There was a significant decrease in the mean Ki-67 staining in the Iex-1 KO animals when compared to WT controls (P<0.05). (i) Representative staining for TUNEL from the outflow vein removed from Iex-1 KO (second column) and WT mice (third column) Negative control was shown where the recombinant terminal deoxynucleotidyl transferase enzyme was omitted in first column. Nuclei staining brown are positive for TUNEL. (j) Pooled data from the semiquantitative analysis for intensity of TUNEL staining in the vessel wall of the outflow vein specimens removed from Iex-1 KO and WT mice are shown. There was a significant decrease in the mean TUNEL staining in the Iex-1 KO animals when compared to WT controls (P<0.05). Two-way Student t-test with post hoc Bonferroni's correction was performed. Significant difference from control value is indicated by * P<0.05. Each bar shows mean±SEM of 4-5 animals per group. For all representative sections * denotes vessel lumen. 40× magnification, scale bar is 100 μms.

DETAILED DESCRIPTION

Figure 2H:
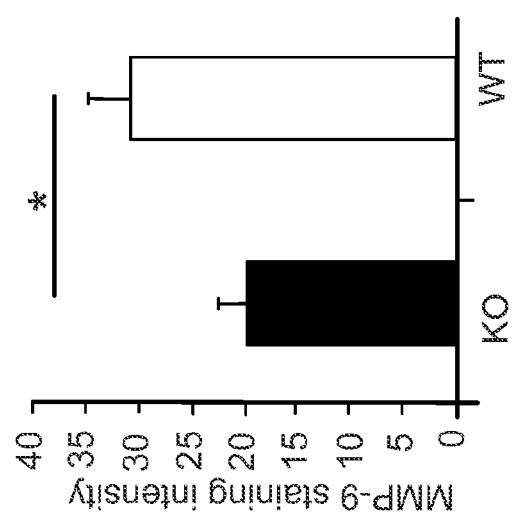
FIG. 2: Gene expression of Vegf-A and Mcp-1 by qRT-PCR at the outflow vein of AVF three days after fistula placement in Iex-1 KO and WT mice. Immunohistochemical staining for VEGF-A, MCP-1, and MMP-9 was performed twenty-eight days after AVF placement in Iex-1 KO and WT mice. (a) Data for Vegf-A expression by qRT-PCR in outflow veins of AVF three days after fistula placement were pooled. There is a significant decrease in the average gene expression of Vegf-A in the Iex-1 KO animals when compared to WT controls (P<0.05). (b) Representative staining for VEGF-A on sections removed from the outflow vein of Iex-1 KO (second column) and WT controls (third column) is shown. IgG antibody staining was performed to serve as negative control in the first column. Brown staining cells are positive for VEGF-A. (c) Data from the semi-quantitative analysis for intensity of VEGF-A staining in the vessel wall of the outflow vein specimens removed from Iex-1 KO and WT mice were pooled. There was a significant decrease in the mean VEGF-A staining in the Iex-1 KO animals when compared to WT controls (P<0.05). (d) Data for the average gene expression of Mcp-1 by qRT-PCR in outflow veins of AVF three days after fistula placement were pooled. There was a significant decrease in the expression of MCP-1 in the Iex-1 KO animals when compared to WT controls (P<0.05). (e) Representative staining for MCP-1 on sections on the outflow vein removed from Iex-1 KO (second column) and WT controls (third column) are shown. IgG antibody staining was performed to serve as negative control in the first column. Brown staining cells are positive for MCP-1. (f) Data from the semiquantitative analysis for intensity of MCP-1 staining in the vessel wall of the outflow vein specimens removed from Iex-1 KO and WT mice were pooled. There was a significant decrease in the mean MCP-1 staining in the Iex-1 KO animals when compared to WT controls (P<0.05). (g) Representative staining for MMP-9 sections from the outflow vein removed from Iex-1 KO (second column) and WT controls (third column) are shown. IgG antibody staining was performed to serve as negative control in the first column. Brown staining cells are positive for MMP-9. (h) Data from the semiquantitative analysis for intensity of MMP-9 staining in the vessel wall of the outflow vein specimens removed from Iex-1 KO and WT mice were pooled. There was a significant decrease in the mean MMP-9 staining in the Iex-1 KO animals when compared to WT controls (P<0.05). For all representative sections * denotes vessel lumen. 40× magnification, scale bar is 100-µms.

This document provides methods and materials for reducing development of stenosis of arteriovenous fistulas. For example, this document relates to reducing IEX-1 polypeptide expression or activity within a mammal (e.g., a human) to reduce venous neointimal hyperplasia and/or the development of stenosis of arteriovenous fistulas. In some cases, a composition that reduces IEX-1 polypeptide expression or activity can be used to reduce venous neointimal hyperplasia and/or to reduce development of stenosis of a hemodialysis vascular access such as an arteriovenous fistula in a mammal. Examples of mammals that can be treated as described herein include, without limitation, humans, monkeys, dogs, cats, cows, horses, pigs, rats, and mice. In some cases, the mammal can be a mammal that requires hemodialysis and has an arteriovenous fistula.

As described herein, venous neointimal hyperplasia and/or the development of stenosis of an arteriovenous fistula can be reduced or slowed by administering a composition that reduces IEX-1 polypeptide expression or activity (e.g., a composition containing an inhibitor of IEX-1 polypeptide expression or activity). Examples of IEX-1 polypeptides include, without limitation, the human polypeptide having the amino acid sequence set forth in GenBank® accession number NP_003888 (GI No. 119964723) and the mouse polypeptide having the amino acid sequence set forth in GenBank® accession number AAO39405 (GI No. 37726925).

A composition that reduces IEX-1 polypeptide expression or activity can include one or more compounds that reduce IEX-1 polypeptide expression, one or more compounds that reduce IEX-1 polypeptide activity, or a combination of one or more compounds that reduce IEX-1 polypeptide expression and one or more compounds that reduce IEX-1 polypeptide activity. Examples of compounds that reduce IEX-1 polypeptide expression include, without limitation, nucleic acid molecules designed to induce RNA interference (e.g., an RNAi molecule or a shRNA molecule), antisense molecules, calcitriol, and miRNAs. Examples of such RNAi molecules and shRNA molecules include, without limitation, those set forth in Table 1. An example of an miRNA that reduces IEX-1 polypeptide expression includes, without limitation, hcmv-miR-UL148D, which is described elsewhere (Wang et al., *Int. J. Mol. Med.*, 31:959-966 (2013)). Examples of compounds that reduce IEX-1 polypeptide activity include, without limitation, anti-IEX-1 polypeptide antibodies.

TABLE 1

Examples of shRNA molecules.

| Sequence | Species | SEQ ID NO: |
|---|---|---|
| ATGTGTCACTCTCGCAGCT | Human | 1 |
| GCTCCGGTCCTGAGATCTT | Human | 2 |
| TCTTTCTGCTGCTCACCAT | Human | 3 |
| CCTTTAATCTGACTTCGGA | Human | 4 |
| GCACTTTCCTCCAGCAACA | Human | 5 |
| ATGTGTCACTCTCGCAGCT | Human | 6 |
| GCTCCGGTCCTGAGATCTTC | Human | 7 |
| TCTTTCTGCTGCTCACCAT | Human | 8 |
| CCTTTAATCTGACTTCGGA | Human | 9 |
| GCACTTTCCTCCAGCAACA | Human | 10 |
| GCAACCATCTCCACACCAT | Mouse | 11 |
| TCCACCGCGCGTTTGAACA | Mouse | 12 |
| TCGCCATCATCTTCTGCCA | Mouse | 13 |
| ACTATGCGCTGGATCTTAA | Mouse | 14 |
| AACATCCGGCGGCCTTCTA | Mouse | 15 |
| GCAACCATCTCCACACCAT | Mouse | 16 |
| TCCACCGCGCGTTTGAACA | Mouse | 17 |
| TCGCCATCATCTTCTGCCA | Mouse | 18 |
| ACTATGCGCTGGATCTTAA | Mouse | 19 |
| AACATCCGGCGGCCTTCTA | Mouse | 20 |

In some cases, an inhibitor of IEX-1 polypeptide expression or activity provided herein can be formulated with other components to form particles containing the inhibitor. For example, particles (e.g., nanoparticles of poly(lactic-co-glycolic) acid; PLGA) can be coated with or conjugated to calcitriol to form a composition containing an inhibitor of IEX-1 polypeptide expression or activity. Examples of particles that can be coated with or conjugated to an inhibitor of IEX-1 polypeptide expression or activity to form a composition provided herein include, without limitation, nanoparticles, gold particles, and poly(lactic-co-glycolic acid) particles.

In some cases, an inhibitor of IEX-1 polypeptide expression or activity provided herein can be chemically converted from its free base form to a pharmaceutically acceptable salt by reacting the free base with an equivalent amount of an acid that forms a non-toxic salt. Such acids can be either inorganic or organic including, without limitation, hydrochloric acid, hydrobromic acid, fumaric acid, maleic acid, succinic acid, sulfuric acid, phosphoric acid, tartaric acid, acetic acid, citric acid, and oxalic acid. In some cases, an inhibitor of IEX-1 polypeptide expression or activity or a pharmaceutically acceptable salt thereof provided herein can be administered to a mammal by itself or in combination with a carrier. Such carriers include, without limitation, sterile aqueous or non-aqueous solutions, suspensions, and emulsions. Examples of non-aqueous solvents include, without limitation, propylene glycol, polyethylene glycol, vegetable oils, and injectable organic esters. Aqueous carriers include, without limitation, water, alcohol, saline, and buffered solutions. In some cases, preservatives, flavorings, and other additives such as, for example, antimicrobials, antioxidants, chelating agents, inert gases, and the like can be present. It will be appreciated that an inhibitor of IEX-1 polypeptide expression or activity or a pharmaceutically acceptable salt thereof provided herein that is to be administered to a mammal can contain zero, one, or more than one commonly known pharmaceutically acceptable carriers.

Any appropriate method can be used to identify or confirm that a compound reduces IEX-1 polypeptide expression or activity. For example, PCR methods (e.g., RT-PCR methods) can be used to determine the levels that IEX-1 mRNA is expressed by cells contacted with a test compound to confirm that the test compound reduced IEX-1 polypeptide expression.

In some cases, one or more than one inhibitor of IEX-1 polypeptide expression or activity can be administered to a mammal with an arteriovenous fistula to reduce venous neointimal hyperplasia and/or to reduce development of stenosis of the arteriovenous fistula. For example, two, three, four, or five different inhibitors of IEX-1 polypeptide expression or activity can be administered in combination or sequentially to a mammal with an arteriovenous fistula to reduce venous neointimal hyperplasia and/or to reduce development of stenosis of the arteriovenous fistula. In some cases, a nucleic acid molecule designed to induce RNA interference (e.g., an RNAi molecule or a shRNA molecule) against an IEX-1 polypeptide can be used in combination with one or more inhibitors of IEX-1 polypeptide activity or in place of an inhibitor of IEX-1 polypeptide activity. For example, an RNAi molecule designed to induce RNA interference against expression of a human IEX-1 polypeptide can be administered in combination with or sequentially with an inhibitor of IEX-1 polypeptide activity (e.g., calcitriol).

A composition or combination of compositions provided herein can be administered to any part of a mammal's body. For example, a composition or combination of compositions provided herein can be administered directly to an arteriovenous fistula of a mammal. In some cases, a composition or combination of compositions provided herein can be administered via an adventitial administration. In some cases, a composition or combination of compositions provided herein can be administered intravenously, subcutaneously, intraperitoneal, or orally.

In some cases, nanoparticles can be coated with calcitriol and delivered to the adventitial or endothelium of an AVF during placement. In other cases, the nanoparticles can be delivered after a stenosis forms and during an angioplasty procedure. In these cases, they can be delivered to the vessel wall.

Nucleic acid molecules designed to induce RNA interference against IEX-1 polypeptide expression can be administered to a mammal using any appropriate method including, without limitation, those methods described herein. For example, a nucleic acid designed to induce RNA interference against IEX-1 polypeptide expression can be administered intravenously to a mammal using a vector such as a viral vector.

Vectors for administering nucleic acids (e.g., a nucleic acid designed to induce RNA interference against IEX-1 polypeptide expression) to a mammal can be prepared using, for example, packaging cell lines, helper viruses, and vector constructs as described elsewhere (*Gene Therapy Protocols* (*Methods in Molecular Medicine*), edited by Jeffrey R. Morgan, Humana Press, Totowa, N.J. (2002) and *Viral Vectors for Gene Therapy: Methods and Protocols*, edited by Curtis A. Machida, Humana Press, Totowa, N.J. (2003)). Virus-based nucleic acid delivery vectors that can be used as described herein can be derived from animal viruses, such as adenoviruses, adeno-associated viruses, retroviruses, lentiviruses, vaccinia viruses, herpes viruses, and papilloma viruses.

Vectors for nucleic acid delivery can be genetically modified such that the pathogenicity of the virus is altered or removed. The genome of a virus can be modified to increase infectivity and/or to accommodate packaging of a nucleic acid, such as a nucleic acid designed to induce RNA interference against IEX-1 polypeptide expression. A viral vector can be replication-competent or replication-defective, and can contain fewer viral genes than a corresponding wild-type virus or no viral genes at all.

In addition to nucleic acid designed to induce RNA interference against IEX-1 polypeptide expression, a viral vector can contain regulatory elements operably linked to a nucleic acid designed to induce RNA interference against IEX-1 polypeptide expression. Such regulatory elements can include promoter sequences, enhancer sequences, response elements, signal peptides, internal ribosome entry sequences, polyadenylation signals, terminators, or inducible elements that modulate expression (e.g., transcription or translation) of a nucleic acid. The choice of element(s) that may be included in a viral vector depends on several factors, including, without limitation, inducibility, targeting, and the level of expression desired. For example, a promoter can be included in a viral vector to facilitate transcription of a nucleic acid designed to induce RNA interference against IEX-1 polypeptide expression. A promoter can be constitutive or inducible (e.g., in the presence of tetracycline), and can affect the expression of a nucleic acid designed to induce RNA interference against IEX-1 polypeptide expression in a general or tissue-specific manner.

As used herein, "operably linked" refers to positioning of a regulatory element in a vector relative to a nucleic acid in such a way as to permit or facilitate expression of the nucleic acid. For example, a viral vector can contain a promoter and a nucleic acid designed to induce RNA interference against IEX-1 polypeptide expression. In this case, the promoter is operably linked to a nucleic acid designed to induce RNA interference against IEX-1 polypeptide expression such that it drives transcription of the nucleic acid.

A nucleic acid designed to induce RNA interference against IEX-1 polypeptide expression also can be administered to cells using non-viral vectors. Examples of methods of using non-viral vectors for nucleic acid delivery are described elsewhere. See, for example, *Gene Therapy Protocols* (*Methods in Molecular Medicine*), edited by Jeffrey R. Morgan, Humana Press, Totowa, N.J. (2002). For example, a nucleic acid designed to induce RNA interference against IEX-1 polypeptide expression can be administered to a mammal by direct injection of nucleic acid molecules (e.g., plasmids) comprising nucleic acid designed to induce RNA interference against IEX-1 polypeptide expression, or by administering nucleic acid molecules complexed with lipids, polymers, or nanospheres.

An effective amount of a compound that reduces IEX-1 polypeptide expression or activity provided herein (e.g., an inhibitor of IEX-1 polypeptide activity such as calcitriol or a nucleic acid molecule designed to induce RNA interference against IEX-1 polypeptide expression) can be administered to a mammal having an arteriovenous fistula to reduce venous neointimal hyperplasia and/or to reduce the development of stenosis of the arteriovenous fistula as described herein. The term "effective" as used herein refers to any amount that induces a desired reduction of IEX-1 polypeptide expression or activity while not inducing significant toxicity in the mammal. Such an amount can be determined using the methods and materials provided herein. Some compounds may have a relatively broad concentration range that is effective, while others may have a relatively narrow effective concentration range. In addition, the effective amount can vary depending upon the specific mammal or the specific condition of an arteriovenous fistula. Such effective amounts can be determined for individual compounds using commonly available or easily ascertainable information involving equilibrium dissociation constants, mammal toxicity concentrations, and bioavailability. For example, non-toxic compounds typically can be directly or indirectly administered to a mammal in any amount that induces a desired level of inhibition of IEX-1 polypeptide expression or activity in that mammal.

Using the information provided herein, such effective amounts also can be determined in vitro or in vivo. For example, a patient can receive direct administration of a compound provided herein in an amount to achieve a blood level close to the equilibrium dissociation constant (i.e., $K_d$) calculated from in vitro analysis sufficient to inhibit IEX-1 polypeptide activity. If the patient fails to respond, then the amount can be increased by, for example, two fold. After receiving this higher concentration, the patient can be monitored for both responsiveness to the treatment and toxicity symptoms, as well as blood levels of the drug, and adjustments made accordingly.

Various factors can influence the actual effective amount used for a particular application. For example, the frequency of administration, duration of treatment, rate of metabolism of the drug, combination of other compounds, and site of administration may require an increase or decrease in the actual effective amount administered.

The frequency of administration can be any frequency that induces a desired reduction of IEX-1 polypeptide expression or activity within a mammal without producing significant toxicity to the mammal. For example, the frequency of administration can be from about twice a day to about once a month, or more specifically, from about once a day to about once a week. In addition, the frequency of administration can remain constant or can be variable during the duration of treatment. As with the effective amount, various factors can influence the actual frequency of administration used for a particular application. For example, the effective amount, duration of treatment, rate of metabolism of the drug, combination of other compounds, and site of administration may require an increase or decrease in administration frequency.

An effective duration for administration of a compound provided herein can be any duration that induces a desired reduction of IEX-1 polypeptide expression or activity within a mammal without producing significant toxicity to the mammal. Thus, the effective duration can vary from several days to several weeks, months, or years. In general, the effective duration for reducing venous neointimal hyperplasia and/or the development of stenosis of a hemodialysis vascular access such as an arteriovenous fistula in a mammal can range in duration from several months to several months. Once the compound administrations are stopped, however, venous neointimal hyperplasia or stenosis of the hemodialysis vascular access may increase or develop.

Multiple factors can influence the actual effective duration used for a particular treatment regimen. For example, an effective duration can vary with the frequency of compound administration, effective compound amount, combination of multiple compounds, and site of administration.

The level of toxicity, if any, can be determined by assessing a mammal's clinical signs and symptoms before and after administering a known amount of a particular composition. It is noted that the effective amount of a particular composition administered to a mammal can be adjusted according to a desired outcome as well as the mammal's response and level of toxicity. Significant toxicity can vary for each particular mammal and each particular composition.

This document also provides methods and materials for reducing development of stenosis in other vascular injury conditions. For example, the methods and materials described herein can be used to reduce IEX-1 polypeptide expression or activity within a mammal (e.g., a human) to reduce venous neointimal hyperplasia and/or the development of arterial stenosis or restenosis (e.g., involving a peripheral bypass or coronary artery bypass graft), after angioplasty, atherectomy, or stent placement. In some cases, a composition provided herein that reduces IEX-1 polypeptide expression or activity can be used to reduce venous neointimal hyperplasia and/or to reduce development of arterial stenosis in a mammal.

The invention will be further described in the following examples, which do not limit the scope of the invention described in the claims.

EXAMPLES

Example 1—IEX-1 Polypeptides are Involved in the Pathogenesis of Venous Neointimal Hyperplasia Associated with Hemodialysis Arteriovenous Fistula Surgical Resection of AVF Tissue Tissue resected during surgical revision or thrombectomy was obtained in paraffin embedded blocks.

Experimental Animals

Animals were kept at 12/12 hour light/dark cycles, 22° C., and 41% relative humidity with access to food and water ad libitum. Anesthesia was induced prior to all procedures using an intraperitoneal injection of ketamine hydrochloride (100 mg/kg) and xylazine (10 mg/kg) and maintained using ketamine hydrochloride (40 mg/kg) and xylazine (15 mg/kg). Chronic kidney disease was induced by removing the right kidney followed by ligation of the blood supply to the upper pole of the left kidney as described elsewhere (Misra et al., *J. Vasc. Interv. Radiol.*, 21:1255-1261 (2010)). Four weeks after nephrectomy, an AVF was created between the carotid artery and the ipsilateral jugular vein. All procedures were performed under dissecting microscope (Zeiss Operating Microscope OPMI 6-SDFC, Oberkochen, Germany) (Yang et al., *Kidney Int.*, 85:289-306 (2014); Janardhanan et al., *Kidney Int.*, 84:338-52 (2013); Yang et al., *J. Vasc. Interv. Radiol.*, 20:946-950 (2009)). Iex-1 knockout and wild type animals were euthanized at days 3 and 28 after the creation of the AVF. The outflow vein was removed and used for qRT-PCR at day 3 and histomorphometric analyses at day 28. Serum BUN and creatinine were measured prior to nephrectomy, at the time of AVF placement and at the time of sacrifice.

For testing the effects of nanoparticles composed of poly (lactic-co-glycolic) acid (PLGA) and coated with calcitriol, C57BL/6 mice were used and underwent nephrectomy followed by the placement of AVF twenty-eight days later as described herein. At the time of AVF creation, animals received either: hydrogel with PLGA, hydrogel with calcitriol plus nanoPLGA, or hydrogel alone. Animals were sacrificed at day 7 for qRT-PCR analysis and day 28 for histomorphometric analysis.

Procedures to Ensure Animal Comfort and Anesthesia

All investigators were required to administer the appropriate analgesics to all animals during a procedure that would normally require pain medication in humans. The mice that undergo surgery for the creation of the AVF procedure were anesthetized by administering anesthesia. All surgical procedures were conducted in a disinfected, uncluttered area, which promotes asepsis during surgery. The animals were maintained at a surgical plane of anesthesia throughout the procedure, and the vital signs were monitored. The surgical incision was closed using appropriate techniques and materials. After surgery, the animal was moved to a warm, dry area and monitored during recovery. Heat lamps or warming pads were used in maintaining or recovering body temperature.

IEX-1 Null Mutant Mouse and Genotyping

The mouse ortholog of the IEX-1 gene is known as Iex-1/gly96. This knockout mouse was created as described elsewhere (Sommer et al., *J. Appl. Physiol.*, 100:707-716 (2006)). These mice are known to have hypertension and endothelial changes such as peliosis in the spleen (Sommer et al., *J. Appl. Physiol.*, 100:707-716 (2006)). Tail veins were removed from the mice at the time of weaning. The Qiagen DNeasy kit (Qiagen, Gaithersburg, Md.) was used to process the tissue. DNA was then amplified using Iex-1 primers and subsequently run out on an agarose gel to determine genotype. Only male Iex-1$^{-/-}$ and WT mice were used.

Tissue Harvesting

At the time of sacrifice, anesthesia was induced as described herein. Mice were euthanized by $CO_2$ asphyxiation. The fistula was dissected free, and specimens were saved for qRT-PCR or histologic analysis as described elsewhere (Yang et al., *Kidney Int.*, 85:289-306 (2014) and Janardhanan et al., *Kidney Int.*, 84:338-52 (2013)).

Calcitriol Loaded Poly (Lactic-Co-Glycolic) Acid (PLGA) Nanoparticles and Hydrogel PLGA nanoparticles were encapsulated with calcitriol using the interfacial deposition method. Briefly, 100 mg of PLGA (Durect, Cupertino, Calif.) and 0.1 µg of calcitriol (Tocris Bioscience, Bristol, UK) were dissolved in 10 mL of acetone. Then, the solution was added drop-wise to deionized water. After particle formation, the organic solvent was evaporated, and the PLGA nanoparticles were dried through lyophilization. The dried PLGA nanoparticles were dispersed in an aqueous solution at a concentration of 200 µM. For the PLGA particles alone, an equivalent portion was made into a 200-µM solution. A 40% solution of pluronic F-127 (Sigma-Aldrich, St. Louis, Mo.) was prepared under sterile conditions at 4° C. Forty grams of pluronic F-127 were added to 100 mL of distilled water. This was placed on a stir plate and allowed to mix overnight at 4° C. This was then mixed with equal parts of 200 µM PLGA or 200 µM of calcitriol plus PLGA solution. This resulted in two solutions of 20% hydrogel at 100 µM, which were kept on ice until the time of surgery. Each animal received of 5 µL of 100 µM calcitriol (208.32 ng) bound to nanoparticle in 20-wt % pluronic gel. At the time of surgery, the solutions were warmed to room temperature before being applied to the adventitia of the outflow vein.

Cell Culture

To determine the expression of Iex-1 and Vegf-A in vitro, NIH 3T3 cells (ATCC, Manassas, Va.) were used and subjected to hypoxia and normoxia for different lengths of time as described elsewhere (Yang et al., *Kidney Int.*, 85:289-306 (2014) and Janardhanan et al., *Kidney Int.*, 84:338-52 (2013)). Cells were harvested for qRT-PCR analysis.

RNA Isolation

Cells or tissue were stored in a RNA stabilizing/cell lysis solution (Qiagen, Gaithersburg, Md.) (Yang et al., *Kidney Int.*, 85:289-306 (2014) and Janardhanan et al., *Kidney Int.*, 84:338-52 (2013)). Specimens were homogenized, and total RNA was extracted and isolated via the miRNEasy Mini kit (Qiagen). Culture cells were trypsinized and stored in Qiazol lysis regent and processed using the RNEasy Mini kit.

qRT-PCR Analysis

Gene expression was quantified using qRT-PCR as described elsewhere (Yang et al., *Kidney Int.*, 85:289-306 (2014) and Janardhanan et al., *Kidney Int.*, 84:338-52 (2013)). Specific primers (Integrated DNA Technologies, Coralville, Iowa) used in this analysis are shown in Table 2.

TABLE 2

Primers.

| Gene | Sequence |
| --- | --- |
| 18S | 5'-AGCTAGGAATAATGGAATAG-3' (sense; SEQ ID NO: 21) 5'-AATCAAGAACGAAAGTCGGAG-3' (antisense; SEQ ID NO: 22) |
| Iex-1 | 5'-GCGCGTTTGAACACTTCTC-3' (sense; SEQ ID NO: 23) 5'-ATGGCGAACAGGAGAAAGAG-3' (antisense; SEQ ID NO: 24) |
| Mmp-9 | 5'-GTTTTTGATGCTATTGCTGAGATCCA-3' (sense; SEQ ID NO: 25) 5'-CCCACATTTGACGTCCAGAGAAGAA-3' (antisense; SEQ ID NO: 26) |
| Mcp-1 | 5'-GTCCCTGTCATGCTTCTGG-3' (sense; SEQ ID NO: 27) 5'-GCTCTCCAGCCTACTCATTG-3' (antisense; SEQ ID NO: 28) |
| Vegf-A | 5'-ATGAAGTGATCAAGTTCATGG-3' (sense; SEQ ID NO: 29) 5'-GGATCTTGGACAAACAAATGC-3' (antisense; SEQ ID NO: 30) |

Tissue Processing and Immunohistochemistry

The outflow vein from each animal was embedded in paraffin lengthwise. Eighty to 120 4-µm sections from each outflow vein from each animal were obtained, and every 40-µm, 2-4 sections were stained with hematoxylin and eosin. In addition, Ki-67, α-SMA, FSP-1, MMP-9, Ly6C, MCP-1, or VEGF-A staining was performed using the EnVision (DAKO, Carpinteria, Calif.) method with a heat-induced antigen retrieval step for 30 minutes at 95° C. in sodium citrate solution. Four nm sections orthogonal to the long axis were taken to show the lumen of the vessel as described elsewhere (Misra et al., *J. Vasc. Interv. Radiol.*, 21:1255-1261 (2010) and Yang et al., *Kidney Int.*, 85:289-306 (2014)). The following antibodies were then used: mouse monoclonal antibody Ki-67 (DAKO, Carpinteria, Calif., 1:400), rabbit polyclonal antibody to mouse for rabbit polyclonal antibody to mouse for Vegf-A (Abcam, 1:600), rabbit polyclonal antibody to mouse for Mmp-9 (Abcam, 1:600), rabbit polyclonal antibody to mouse for Fsp-1 (Abcam, 1:600), rabbit polyclonal antibody to mouse for α-SMA (Abcam, 1:600), rabbit polyclonal antibody to mouse for MCP-1 (Abcam, 1:600), and rabbit polyclonal antibody to mouse for Ly6C (Abcam, Cambridge, Mass.; 1:400). IgG antibody staining (1:200) was performed to serve as a control.

TUNEL

TUNEL (TdT-mediated dNTP nick end labeling assay) was performed on paraffin-embedded sections from the outflow vein of Iex-1 KO or WT as specified by the manufacturer (DeadEnd Colorimetric tunnel assay system, G7360, Promega, Madison, Wis.). Negative controls were used when the recombinant terminal deoxynucleotidyl transferase enzyme was not used.

Morphometric and Image Analysis

Sections that were immunostained with hematoxylin and eosin were viewed using a Neo-Fluor x 20/0.50 objective lens on an Axioplan 2 Microscope (Zeiss, Oberkochen, Germany) (Yang et al., *Kidney Int.*, 85:289-306 (2014) and Janardhanan et al., *Kidney Int.*, 84:338-52 (2013)).

Statistical Analysis

Data were expressed as mean±SEM. Multiple comparisons were performed with two-way ANOVA followed by Student t-test with post hoc Bonferroni's correction. Significant difference from control value was indicated by *$P<0.05$. JMP version 9 (SAS Institute Inc., Cary, N.C.) was used for statistical analyses.

Results

IEX-1 Expression was Significantly Increased in Failed Clinical Samples of AVF

The expression of IEX-1 in malfunctioning hemodialysis vascular access remains unknown. The expression of IEX-1 was analyzed using immunostaining in venous samples removed from patients with AVFs due to infection, thrombosis, or stenosis (n=3, 2M, average age=58.7+10.6 years old) and compared to control veins removed from patients (n=3, 2M, average age=60+2.6 years old) undergoing placement of AVF (FIG. 1a). There was a significant increase in the mean expression of IEX-1 in AVF when compared to controls (FIG. 1b, average increase: 133%, 6+1.2 vs. 4.4+0.2, P<0.05, venous stenosis vs. control veins). Expression of IEX-1 was localized to the adventitia of the vein (arrow).

Surgical Outcomes

A strain of C57BL/6 mice that had a double allele knockout for the Iex-1 gene as described elsewhere (Sommer et al., *J. Appl. Physiol.*, 100:707-716 (2006)) was used. Only male mice with the following genotype were used: Iex-1$^{-/-}$ and Iex-1$^{+/+}$ (wild type, WT) mice. A total of 36 mice, liter and age matched, weighing 20-25 g had CKD induced by nephrectomy and a carotid artery to jugular AVF placed four weeks later as described elsewhere (Yang et al.,

*Kidney Int.,* 85:289-306 (2014) and Janardhanan et al., *Kidney Int.,* 84:338-52 (2013)). Of the 36 mice, one mouse died after nephrectomy, and two had a thickened artery that precluded the animals from having an AVF placed. Thirty-three mice [Iex-1$^{-/-}$ (n=17) and wild type [Iex-1$^{+/+}$ (n=16)] underwent AVF placement. Of these mice, 11 mice [Iex-1$^{-/-}$ (n=6) and wild type Iex-1$^{+/+}$ (n=5)] were sacrificed at day 3 for qRT-PCR analysis, and twenty-two mice [Iex-1$^{-/-}$ (n=11) and wild type Iex-1$^{+/+}$ (n=11)] were sacrificed at day 28 for histomorphometric and immmuno-histochemical analysis.

The efficacy of a modulator of Iex-1, calcitriol, was tested to determine if it prevented AVF stenosis by loading calcitriol onto nanoparticles composed of PLGA. The efficacy of calcitriol in reducing Iex-1 expression using qRT-PCR was determined in C57BL/6 mice with established CKD and AVF by delivering the drug to the adventitia of the outflow vein at the time of AVF creation. This approach is similar to that describing the delivery of lentiviral tagged shRNA inhibitors to the adventitia (Yang et al., *Kidney Int.,* 85:289-306 (2014) and Nieves et al., *PLoS One,* 9:e94510 (2014)). Twenty-two C57BL/6 male mice, 20-25 g, had CKD induced followed by a AVF placed to connect the carotid artery to the jugular vein twenty-eight days later. Animals were sacrificed at day 7 for qRT-PCR analysis (hydrogel alone, hydrogel with PLGA plus Calcitriol, or hydrogel with PLGA alone) and day 28 for histomorphometric analysis (hydrogel alone and hydrogel with Calcitriol plus PLGA).

Serum BUN, Creatinine, and Blood Pressure

There was no difference in the kidney function (BUN or creatinine) or blood pressure at baseline, after nephrectomy, or at AVF placement between the different groups of animals used.

Iex-1$^{-/-}$ Mice have Decreased Gene Expression of Vegf-A and Mcp-1 at 3 Days after AVF Placement The gene expression of Vegf-A and Mcp-1 on venous stenosis removed from Iex-1$^{-/-}$ and WT controls at 3 days after AVF placement and protein expression using immunostaining at 28 days was determined. The average gene expression of Iex-1 was significantly reduced in Iex-1$^{-/-}$ mice when compared to WT controls (average decrease: 96%, 0.04+0.02 vs. 1+0.22, Iex-1$^{-/-}$ vs. WT, respectively, P<0.05). The average gene expression of Vegf-A in outflow vein removed from Iex-1$^{-/-}$ mice was compared to WT, and it was significantly decreased in the Iex-1$^{-/-}$ mice when compared to WT (average decrease: 34%, 0.66+0.21 vs. 1.0+0.17, Iex-1$^{-/-}$ vs. WT, respectively, P<0.05, FIG. 2a) Immunostaining for VEGF-A (FIG. 2b) was assessed at day 28, which demonstrated that the average VEGF-A staining also was significantly reduced in the Iex-1$^{-/-}$ mice when compared to WT controls (average decrease: 27%, 22.3+2.3 vs. 30.5+3.9, respectively, P<0.05, FIG. 2c).

Next, the levels of MCP-1 were determined. The gene expression of Mcp-1 was significantly reduced in Iex-1$^{-/-}$ mice when compared to WT controls (average decrease: 66%, 0.34+0.2 vs. 1+0.37, Iex-1$^{-/-}$ vs. WT, respectively, P<0.05, FIG. 2d). The average MCP-1 staining (FIG. 2e) was significantly reduced in the Iex-1$^{-/-}$ mice when compared to WT controls (average decrease: 27%, 22.3+2.3 vs. 30.5+3.9, respectively, P<0.05, FIG. 2f).

Figure 2G:
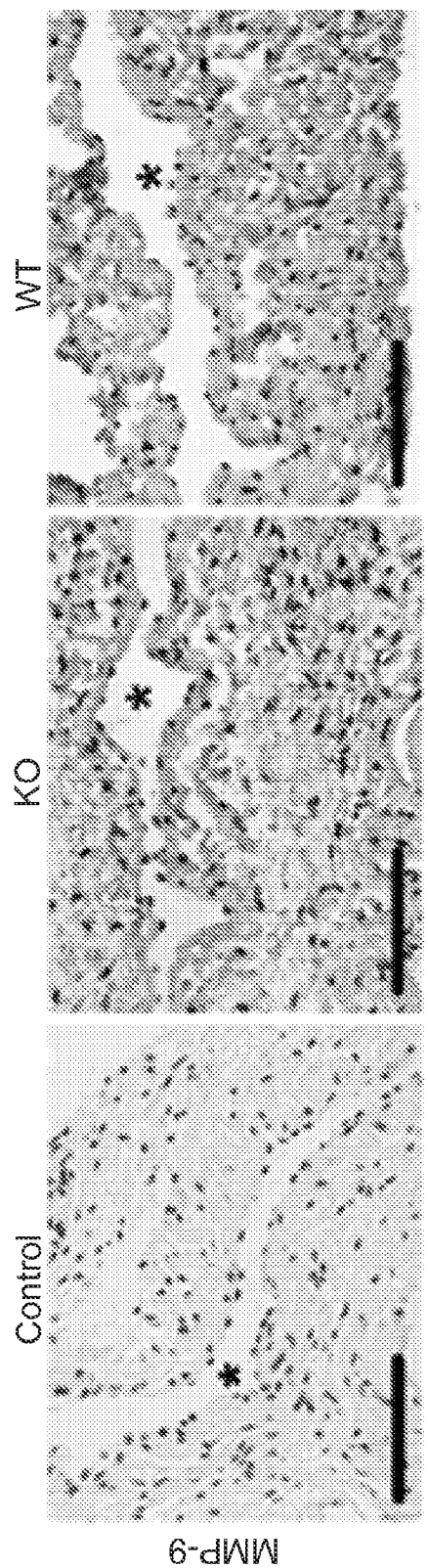

There was no difference in the gene expression of Mmp-9 at day 3 in the Iex-1$^{-/-}$ mice when compared to WT controls. However, there was a significant decrease in the average MMP-9 staining (FIG. 2g) in venous stenosis removed from Iex-1$^{-/-}$ mice when compared to WT controls (average decrease: 35%, 19.8+2.7 vs. 30.6+4.5, Iex-1 KO vs. WT, respectively <0.05, FIG. 2h).

Outflow Veins Removed from Iex-1$^{-/-}$ Mice have Decreased Neointima Area, Decreased Cell Density, and Increased Lumen Vessel Area Histomorphometric analysis of outflow veins removed from Iex-1$^{-/-}$ and WT mice were evaluated twenty-eight days after fistula placement. Using hematoxylin and eosin staining, one could differentiate between the neointima (n) and media and adventitia (m+a, FIG. 3a). The mean lumen vessel area was significantly increased in the Iex-1$^{-/-}$ mice when compared to WT controls (average increase: 144%, respectively, P<0.05, FIG. 3b) with a significant decrease in the average area of the neointima (average decrease: 20%, P<0.05, FIG. 3c). In addition, there was a significant increase in the average area of the media and adventitia (average increase: 201%, Iex-1$^{-/-}$ vs. WT, respectively, P<0.05, FIG. 3d). The average cell density was significantly decreased in the neointima of Iex-1$^{-/-}$ mice when compared to WT controls (average reduction: 25%, P<0.05, FIG. 3e), while in the media and adventitia, there was a 155% increase in the Iex-1$^{-/-}$ mice when compared to WT controls (P<0.05, FIG. 3f).

Decreased Levels of Fibroblasts and Myofibroblasts

Fibroblast specific protein-1 (FSP-1), a marker for fibroblasts, was used to determine if the fibroblast density was decreased in Iex-1$^{-/-}$ mice when compared to WT controls (FIG. 4a). Brown staining cells were positive for FSP-1. The average FSP-1 staining was significantly lower in the venous stenoses removed from Iex-1$^{-/-}$ mice when compared to WT controls (average decrease: 31%, 8.85+2.41 vs. 12.8+4.1, Iex-1$^{-/-}$ vs. WT, respectively, P<0.05, FIG. 4b). Myofibroblasts, α-smooth muscle actin positive cells (α-SMA (+)), were implicated in AVF failure (Yang et al., *Kidney Int.,* 85:289-306 (2014); Janardhanan et al., *Kidney Int.,* 84:338-52 (2013); Wang et al., *Nephrol. Dial. Transplant.,* 22:3139-3146 (2007); and Misra et al., *Kidney Int.,* 68:2890-2900 (2005)). The number of such cells (brown staining cells, FIG. 4c) present in AVF venous stenoses was assessed using immunostaining. There was a significant decrease in the average α-SMA staining cells present in venous stenoses removed from Iex-1$^{-/-}$ mice when compared to WT controls (average decrease: 31%, 23.2+1.2 vs. 28.7+2.5, Iex-1$^{-/-}$ vs. WT, respectively, P<0.05, FIG. 4d). This change was localized primarily to the neointima. Smooth muscle heavy chain or smoothelin staining was assessed, and no difference between the two groups was observed. Also, the samples were assessed for the presence of monocytes using Ly6C immunostaining (FIG. 4e). There was a significant decrease in the average Ly6C staining cells present in venous stenoses removed from Iex-1$^{-/-}$ mice when compared to WT controls (average reduction: 48%, 20+6.9 vs. 38.4+8.4, Iex-1$^{-/-}$ vs. WT, respectively, P<0.05, FIG. 4f).

Iex-1 Knockout Mice have Decreased Proliferation and Increased Apoptosis at 28 Days after AVF Placement Cellular proliferation was increased in venous stenosis formation, and Iex-1 was involved in proliferation. This was assessed using Ki-67 (nuclei staining brown) staining 28 days after AVF placement (Janardhanan et al., *Kidney Int.,* 84:338-52 (2013); and Schulze et al., *Circ. Res.,* 93:1210-1217 (2003)). This revealed that the average Ki-67 index (FIG. 4g) among the Iex-1$^{-/-}$ group was significantly lower than the WT controls (average decrease: 69%, 1.6+0.14 vs. 6.8+0.3, Iex-1$^{-/-}$ vs. WT, respectively, P<0.001, FIG. 4h). Next, TUNEL (TdT-mediated dNTP nick end labeling) staining was used since Iex-1 is involved in apoptosis. This revealed a significant increase in the number of TUNEL positive cells (nuclei staining brown, FIG. 4i) among the venous stenosis removed from Iex-1$^{-/-}$ mice when compared to WT controls (average increase: 157%, 21.4+2.6 vs. 13.6+1.8, P<0.05, respectively, FIG. 4*j*). Overall, these results indicate that venous stenosis removed from Iex-1$^{-/-}$ mice exhibited decreased proliferation and increased apoptosis when compared to WT controls.

Iex-1 and Vegf-A Gene Expression is Increased in Hypoxic Fibroblasts

Figure 5A:
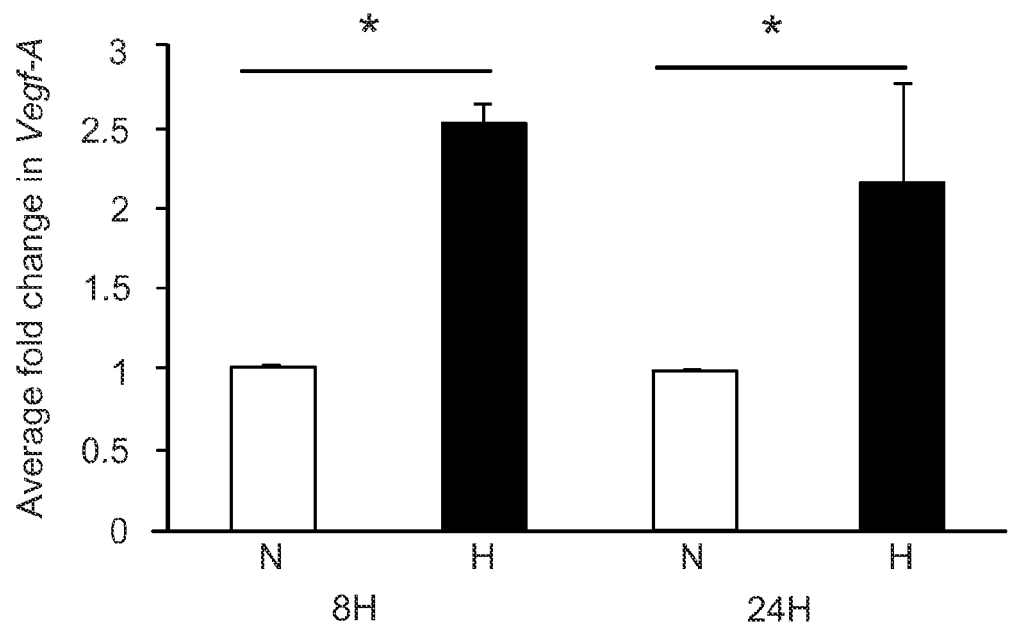
FIG. 5: Vegf-A and Iex-1 expression in hypoxic NIH 3T3 cells. Pooled data for Vegf-A (a) and Iex-1 (b) expression by qRT-PCR in NIH 3T3 cells at 8 hours (8H) and 24 hours (24H) of normoxia (N) and hypoxia (H) are shown. (a) Average Vegf-A gene expression normalized to normoxia at the same time point. (b) Average Iex-1 gene expression normalized to normoxia at the same time point. There was a significant increase in both the average Vegf-A and Iex-1 expression in hypoxic fibroblasts when compared to normoxic (both time points, P<0.05). The average Vegf-A expression was increased in hypoxia when compared to normoxia at 8 and 24 hours (both time points, P<0.05). (c) Iex-1 expression by qRT-PCR in NIH 3T3 cells under normoxia (N) and hypoxia (H) at 24 hours with PBS alone (C) and calcitriol (CT, 1 μM). There is a decrease in the average Iex-1 expression in C vs. CT in the hypoxia group (P<0.05). (d) Pooled data for Iex-1 and Vegf-A expression by qRT-PCR in NIH 3T3 cells at 24 hours of control (C, nano PLGA alone) or Calcitriol (P+CT, 10 μM loaded onto nanoPLGA) of normoxia (N) and hypoxia (H) are shown in (d). There was a significant decrease in both Iex-1 and Vegf-A gene expression in fibroblasts treated with nano-PLGA particles coated with calcitriol when compared to controls (P<0.05). Each bar shows the mean±SEM of 3 samples per group. Two-way Student t-test with post hoc Bonferroni's correction was performed. Significant difference from control value is indicated by * P<0.05.
Figure 5B:
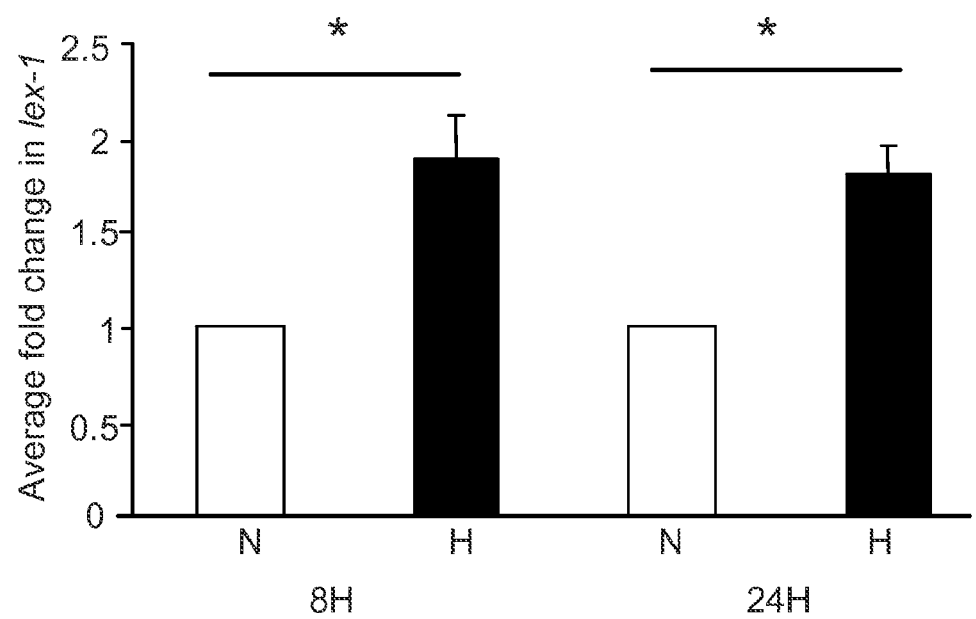

A hypoxic fibroblast model was used elsewhere to understand the mechanisms contributing to VNH formation (Misra et al., *J. Vasc. Interv. Radiol.*, 21:896-902 (2010); and Janardhanan et al., *Kidney Int.*, 84:338-52 (2013)). Using this model, the expression of Iex-1 and Vegf-A at 8 and 24 hours of hypoxia and normoxia was determined. This demonstrated that there was a significant increase in both Iex-1 and Vegf-A gene expression at 8 and 24 hours of hypoxia when compared to normoxia (Vegf-A: 8 h, average increase: 253%, 2.53+0.1 vs. 1.0+0.00, Hypoxia vs. Normoxia, respectively, P<0.05, 24 h: average increase: 220%, 2.2+0.6 vs. 1.0+0.00, Hypoxia vs. Normoxia, respectively, P<0.05, FIG. 5*a*, Iex-1: 8 h, average increase: 150%, 1.5+0.2 vs. 1.0+0.02, Hypoxia vs. Normoxia, respectively, P<0.05, 24 h: average increase: 230%, 2.3+0.2 vs. 1.0+0.02, Hypoxia vs. Normoxia, respectively, P<0.05, FIG. 5*b*).

Calcitriol Reduces Iex-1 and Vegf-A Expression in Hypoxic NIH 3T3

Figure 5C:
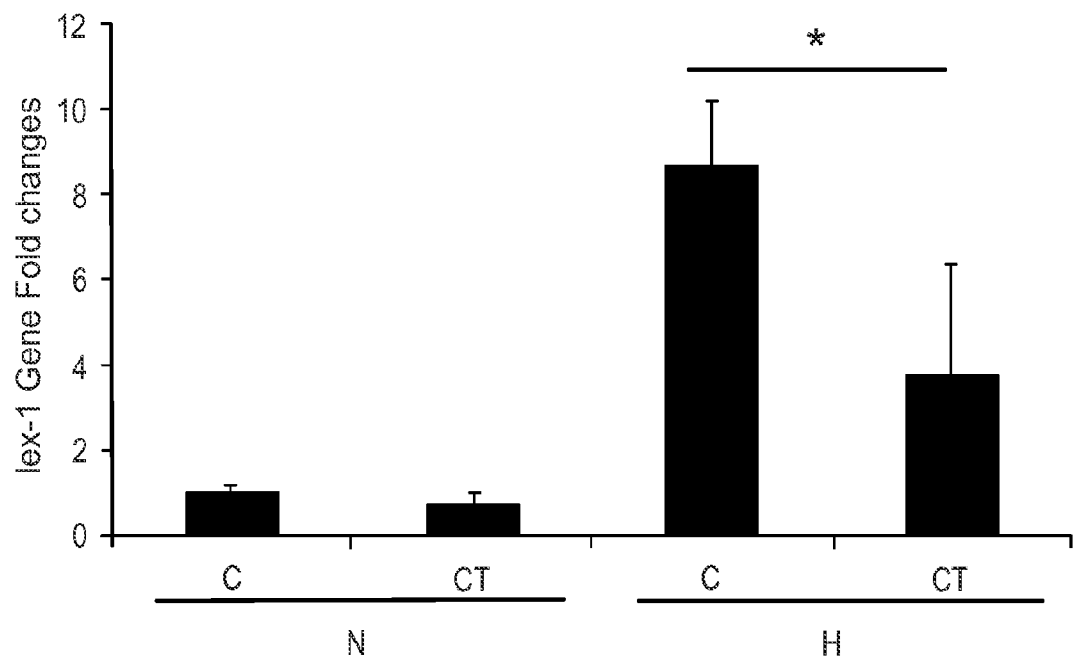
Figure 5D:
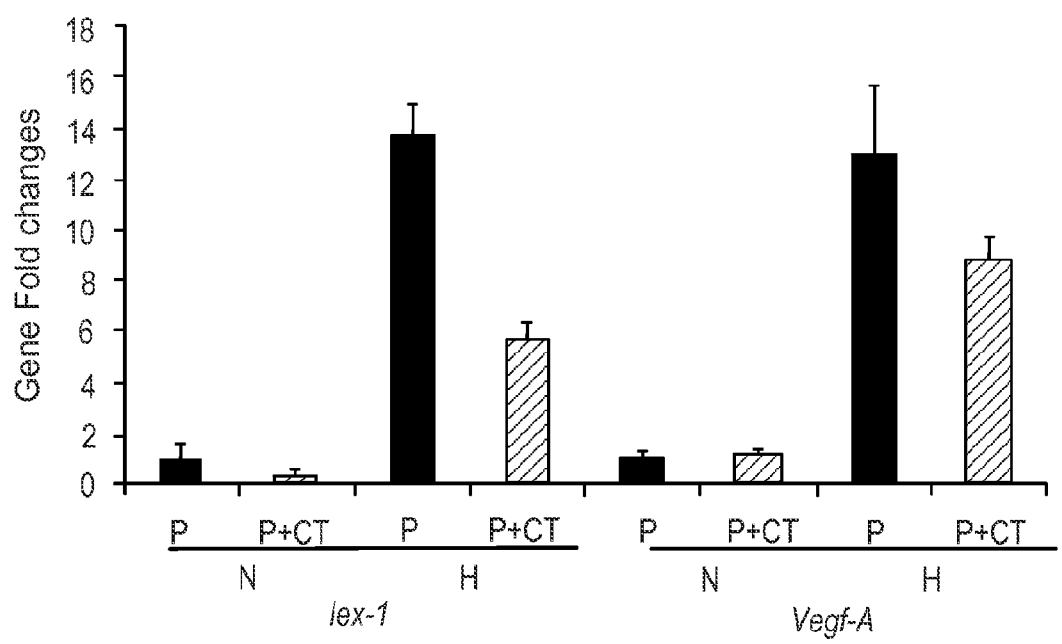
Figure 8:
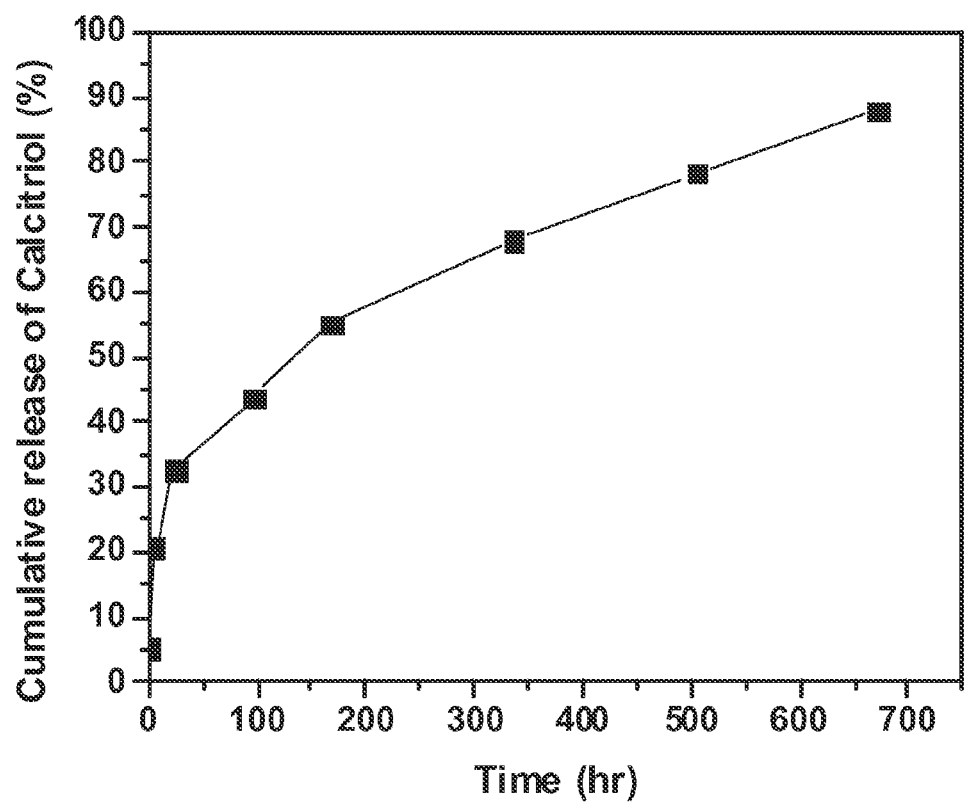
FIG. 8. Calcitriol elution curve from nanoparticle coated PLGA over time.

Calcitriol decreases gene expression of Iex-1 (Im et al., *Oncogene*, 21:3706-3714 (2002); Beer et al., *J. Clin. Oncol.*, 25:669-674 (2007); and Beer et al., *Semin. Oncol.*, 28:49-55 (2001)). The optimal dose of calcitriol required to reduce Iex-1 expression, 1 µM, was determined using a dose response curve (FIG. 8). Using 1 µM of calcitriol, the gene expression of Iex-1 was determined in hypoxic fibroblasts compared to controls at 24 hours. This demonstrated that there was a significant decrease in the average Iex-1 expression in calcitriol treated cells when compared to controls (average decrease: 56%, 3.84+2.2 vs. 8.62+1.52, P<0.05, FIG. 5*c*). Next, calcitriol was loaded in nanoparticles composed of PLGA, and the elution characteristics over time were determined, which demonstrated that calcitriol was eluting for up to 4-weeks. The use of these nanoparticle-loaded calcitriol was compared to controls in hypoxic NIH 3T3, and the gene expression of Iex-1 and Vegf-A was determined. This demonstrated a significant reduction in both the mean Iex-1 and Vegf-A gene expression in hypoxic fibroblasts treated with nano PLGA coated calcitriol compared with controls (Iex-1: average decrease: 58%, 5.6+0.64 vs. 13.7+1.3, P<0.05, Vegf-A: average decrease: 33%, 8.74+0.92 vs. 12.9+2.81, P<0.05, FIG. 5*d*).

Adventitial Delivery of Calcitriol to the Outflow Vein of AVF Reduces Iex-1, Vegf-A, and Mcp-1 Expression 7 Days Later with Significant Reduction in the Neointima Area at Day 28

Figure 6A:
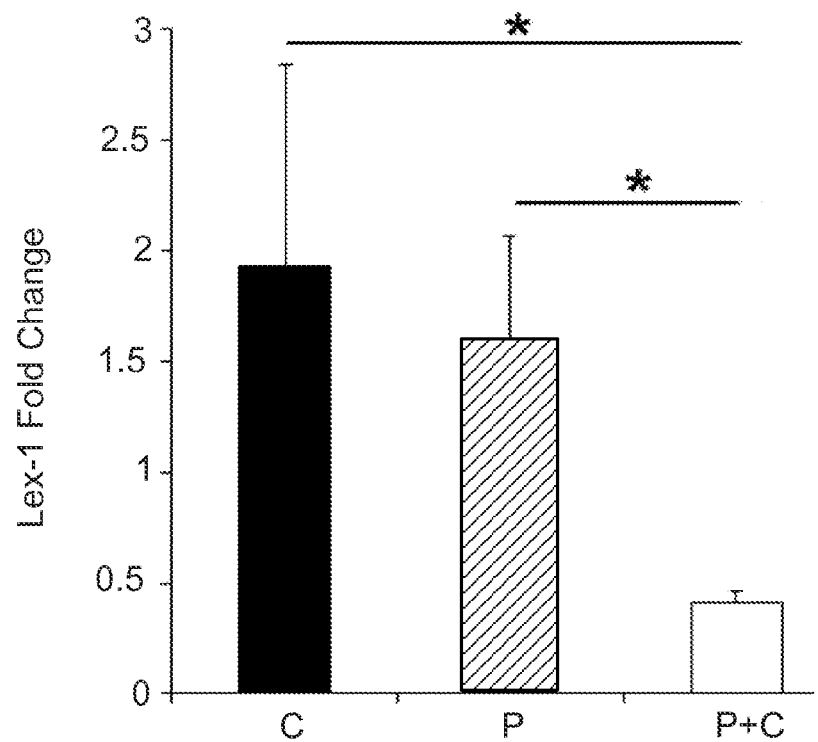
FIG. 6: Gene expression of Iex-1 and Vegf-A by qRT-PCR in outflow vein of AVF seven days after adventitial delivery of hydrogel alone, hydrogel with nanoparticle PLGA without calcitriol, or hydrogel with calcitriol in nanoparticle PLGA. (a) Pooled data for Iex-1 expression by qRT-PCR in outflow veins of AVF seven days after adventitial delivery of hydrogel alone (C), hydrogel with nanoparticle PLGA without calcitriol (P), or hydrogel with calcitriol in nanoparticle PLGA (100 μM, P+C) are shown. This demonstrates a significant decrease in the mean Iex-1 expression in nanoparticle coated with calcitriol compared to PLGA (P<0.05). (b) Pooled data for Vegf-A expression by qRT-PCR in outflow veins treated of AVF seven days after adventitial delivery of hydrogel alone (C), hydrogel with nanoparticle PLGA without calcitriol (P), or hydrogel with calcitriol in nanoparticle PLGA (100 μM, P+C) are shown. This demonstrates a significant decrease in the mean Vegf-A gene expression in nanoparticle coated with calcitriol compared to PLGA alone (P<0.05). (c) Representative hematoxylin and eosin staining of the outflow vein removed from PLGA (P) and PLGA+Calcitriol (P+C) from 28 days after fistula placement. The neointima (n) was identified from the media and adventitia by the dotted line. m+a is the media and adventitia. * indicates lumen. 40× magnification, scale bar is 100 μms. (d) Neointima area/Media+adventitia area ratios for the P and P+C group are shown. There was a significant reduction in the average neointima area in the calcitriol treated vessels when compared to PLGA alone (P<0.05). Two-way Student t-test with post hoc Bonferroni's correction was performed. Significant difference from control value is indicated by * P<0.05. Each bar shows mean±SEM of 4-6 animals per group.
Figure 6B:
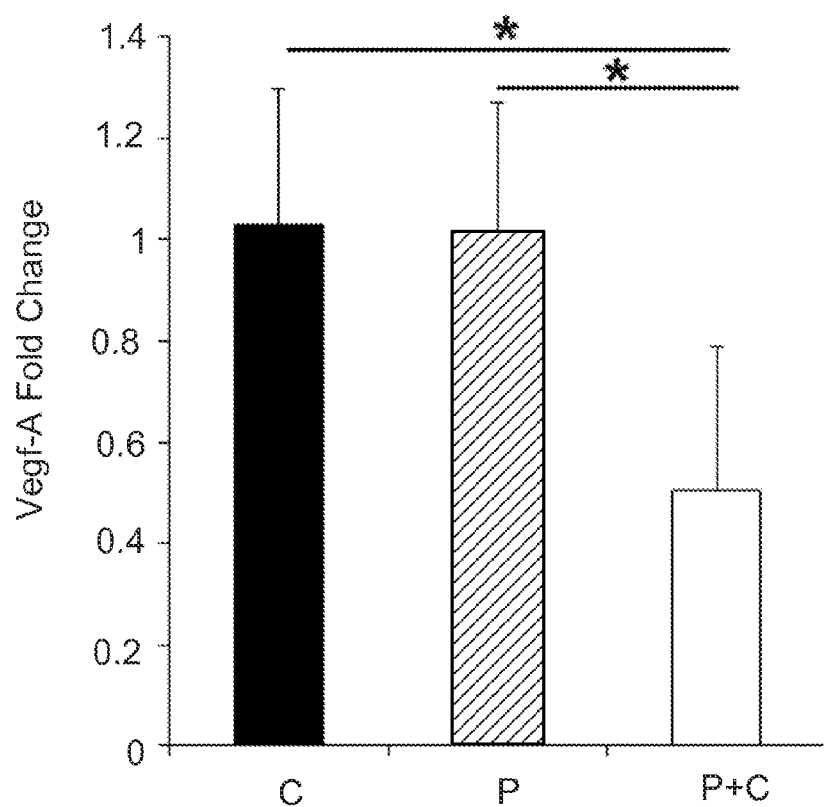

Adventitial delivery of nanoparticle composed of PLGA coated with calcitriol to the outflow vein of AVF placed in mice with established CKD was performed to assess the expression of Iex-1. At 7 days after AVF placement, there was a significant reduction in the mean Iex-1 gene expression in nanoparticle PLGA coated calcitriol when compared to controls (average decrease: 35%, 0.42+0.01 vs. 1.7+0.01 vs. 2.67+0.01, PLGA+Calcitriol, PLGA, and PBS, respectively, P<0.05, FIG. 6*a*). In addition, a significant decrease in the Vegf-A expression was observed (average decrease: 35%, 0.42+0.01 vs. 1.7+0.01 vs. 2.67+0.01, PLGA+Calcitriol, PLGA, and PBS, respectively, P<0.05, FIG. 6*b*). Overall, these results indicate that calcitriol can be used to decrease Iex-1 expression in both in vitro and in vivo and therefore can be used as a translational therapy for reducing IEX-1 expression.

Figure 6C:
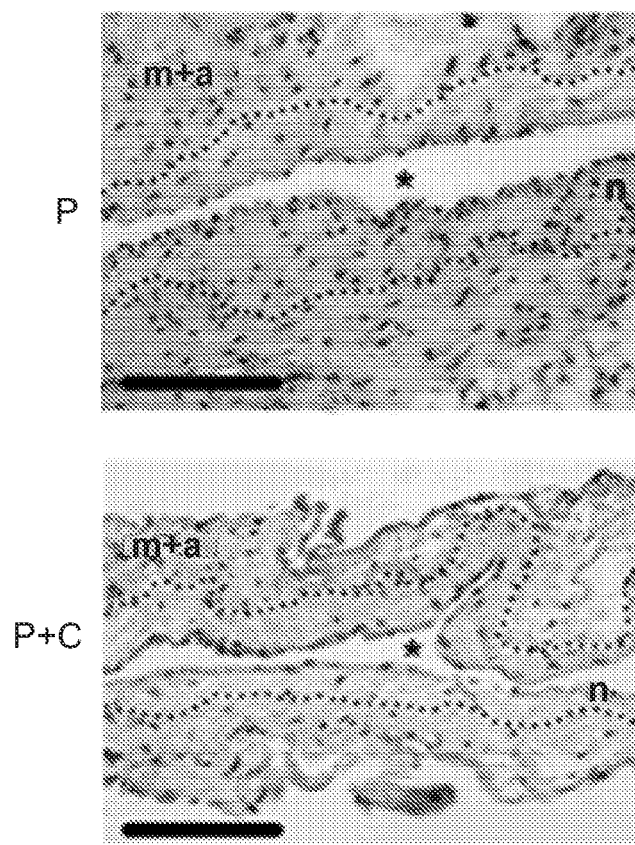
Figure 6D:
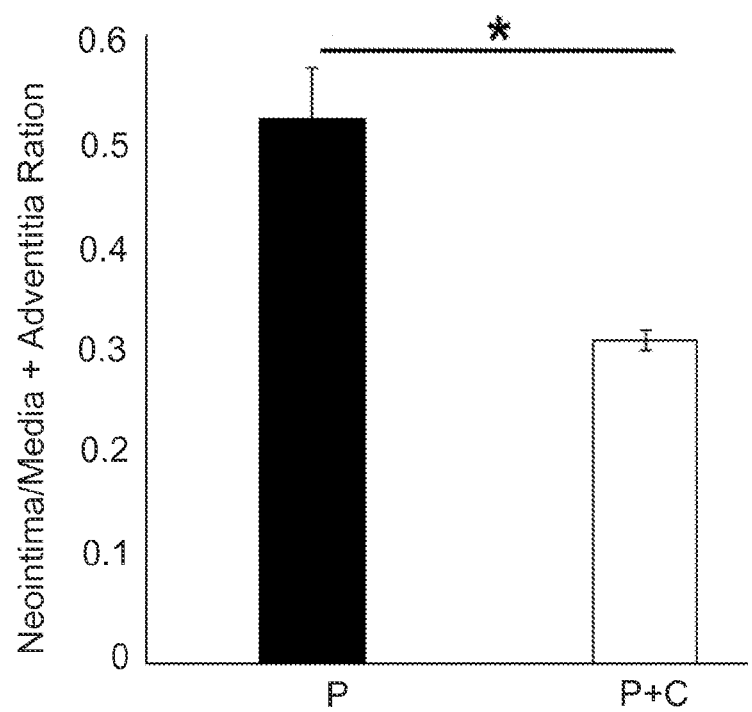

The changes in the venous outflow vein were assessed using histomorphometric analysis at day 28. This demonstrated that there was a significant reduction in the average neointima to media plus adventitia ratio in the calcitriol treated vessels when compared to PLGA alone (average decrease: 34%, PLGA+Calcitriol vs. PLGA, respectively, P<0.05, FIGS. 6*c* and *d*).

Figure 7:
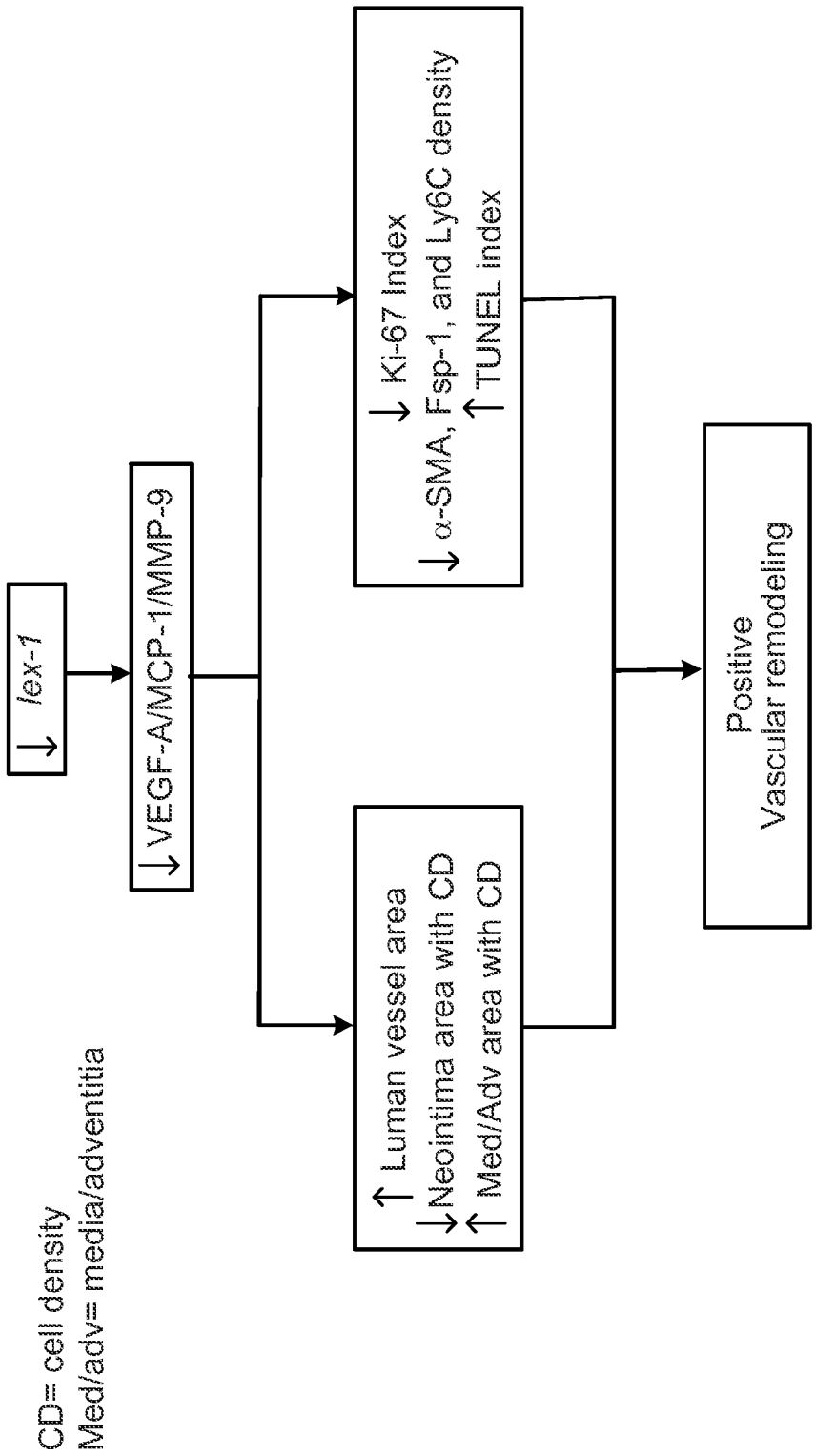
FIG. 7 is a synopsis of the findings.

These results demonstrate that Iex-1 is involved in VNH associated with AVF. By eliminating or reducing Iex-1 expression, AVF patency can be extended by reducing inflammatory and angiogenic responses to cell stress. Decreasing these responses through Iex-1 can reduce Vegf-A/Mcp-1 and MMP-9 mediated VNH (FIG. 7). These changes can result in a decrease in proliferation, an increase in apoptosis, and increased positive vascular remodeling. These results also demonstrate that reducing Iex-1 polypeptide expression or activity can reduce VNH in patients with AVF among the ESRD population.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for reducing the development of stenosis of a surgically created arteriovenous fistula within a mammal, wherein said method comprises administering a composition that reduces IEX-1 polypeptide expression or activity to said mammal, wherein the development of stenosis of said arteriovenous fistula is reduced following said administering step as compared to the level of arteriovenous fistula stenosis development within a mammal having an arteriovenous fistula and not administered said composition, and wherein said composition comprises calcitriol.

2. The method of claim 1, wherein said mammal is a human.

3. The method of claim 1, wherein said composition comprises nanoparticles.

4. The method of claim 1, wherein said composition comprises PLGA nanoparticles.

5. The method of claim 1, wherein between about 5 and 95 percent of said composition comprises calcitriol.

6. The method of claim 1, wherein said composition further comprises gold particles or poly(lactic-co-glycolic acid).

7. The method of claim 1, wherein said administration comprises an adventitial administration.

8. A method for treating a mammal having a surgically created arteriovenous fistula, wherein said method comprises:

(a) identifying said mammal as having said arteriovenous fistula in need of developing less stenosis, and (b) administering a composition that reduces IEX-1 polypeptide expression or activity to said mammal, wherein the development of stenosis of said arteriovenous fistula is reduced following said administering step as compared to the level of arteriovenous fistula stenosis development within a mammal having an arteriovenous fistula and not administered said composition, and wherein said composition comprises calcitriol.

9. The method of claim 8, wherein said mammal is a human.

10. The method of claim 8, wherein said composition comprises nanoparticles.

11. The method of claim 8, wherein said composition comprises PLGA nanoparticles.

12. The method of claim 8, wherein between about 5 and 95 percent of said composition comprises calcitriol.

13. The method of claim 8, wherein said composition further comprises gold particles or poly(lactic-co-glycolic acid).

14. The method of claim 8, wherein said administration comprises an adventitial administration.

* * * * *